(12) United States Patent
Hu et al.

(10) Patent No.: US 9,624,424 B2
(45) Date of Patent: Apr. 18, 2017

(54) LARGE STOKES SHIFT DYES

(71) Applicant: LIFE TECHNOLOGIES CORPORATION, Carlsbad, CA (US)

(72) Inventors: Yi-Zhen Hu, Eugene, OR (US); Hee Chol Kang, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/566,166

(22) Filed: Dec. 10, 2014

(65) Prior Publication Data
US 2015/0090936 A1    Apr. 2, 2015

Related U.S. Application Data

(63) Continuation of application No. 13/148,913, filed as application No. PCT/US2010/023793 on Feb. 10, 2010, now abandoned.

(60) Provisional application No. 61/151,757, filed on Feb. 11, 2009.

(51) Int. Cl.
| | | |
|---|---|---|
| C07D 403/06 | (2006.01) |
| C07D 413/06 | (2006.01) |
| C07D 417/06 | (2006.01) |
| C09K 11/06 | (2006.01) |
| C07D 209/14 | (2006.01) |
| C07D 401/14 | (2006.01) |
| C09B 23/01 | (2006.01) |
| C09B 23/08 | (2006.01) |
| G01N 33/52 | (2006.01) |
| C07D 209/26 | (2006.01) |
| C07D 401/10 | (2006.01) |
| C07H 19/207 | (2006.01) |

(52) U.S. Cl.
CPC ............ *C09K 11/06* (2013.01); *C07D 209/14* (2013.01); *C07D 209/26* (2013.01); *C07D 401/10* (2013.01); *C07D 401/14* (2013.01); *C07H 19/207* (2013.01); *C09B 23/0041* (2013.01); *C09B 23/0066* (2013.01); *C09B 23/086* (2013.01); *G01N 33/52* (2013.01)

(58) Field of Classification Search
None
See application file for complete search history.

(56) References Cited

U.S. PATENT DOCUMENTS

| | | | |
|---|---|---|---|
| 6,180,086 B1 | 1/2001 | Achilefu et al. |
| 6,335,450 B1 | 1/2002 | Farooqui et al. |
| 6,593,148 B1 | 7/2003 | Narayanan |
| 7,488,468 B1 | 2/2009 | Miwa |
| 2008/0206886 A1 | 8/2008 | Wang et al. |

FOREIGN PATENT DOCUMENTS

| | | |
|---|---|---|
| CN | 1702118 A | 11/2005 |
| CN | 1844119 A | 10/2006 |
| CN | 101149373 A | 3/2008 |
| WO | WO-99/49082 | 9/1999 |
| WO | WO-2007/044866 A2 | 4/2007 |
| WO | WO-2008/099914 A1 | 8/2008 |
| WO | WO-2008/108074 A1 | 9/2008 |
| WO | WO-2009/006443 A1 | 1/2009 |
| WO | WO-2010/093726 A8 | 8/2010 |
| WO | WO-2010093726 | 8/2010 |
| WO | WO-2010/093726 A3 | 3/2011 |

OTHER PUBLICATIONS

Bertolino, Chiara et al., "Novel Heptamethine Cyanine Dyes with Large Stokes Shi ft for Biological Applications in the Near Infrared", *J.Fluoresc.*; vol. 16, 2006,, 221-225.
Bhushan, K. et al., "Microwave-assisted synthesis of near-infrared fluorescent sphingosine derivatives", *Chemical Communication*, 37, 2008, pp. 4419-4421.
Descalzo, A. et al., "On the Signalling Pathways and Cu II-Mediated Anion Indication of N-meso-Substituted Heptamethine Cyanine Dyes", *Chem. Eur. J.*, 15, 2009, pp. 3173-3185.
EP 10741680.2, , "Supplementary European Search Report", May 6, 2013, 8 pgs.
Flanagan, J et al., "Functionalized Tricarbocyanine Dyes as near Infrared Fluorescent Probes for Biomolecules", *Bioconjug. Chem.*, vol. 8, 1997, pp. 751-756.
Kiyose, K. , "Development of a Ratiometric Fluorescent Zinc Ion Probe in Near-Infrared Region, Based on Tricarbocyanine Chromophore", *J. Am. Chem. Soc.*, 128, 2006, pp. 6548-6549.
Lim, J. et al., "Polymethine and squarylium molecules with large excited-state absorption", *Chemical Physics* 245, 1999, pp. 79-97.
Medintz, Igor L. et al., "Self-assembled nanoscale biosensors based on quantum dot FRET donors", *Nature Materials*, vol. 2, 2003, 630-638.
Ornelas, C. et al., "Combining Aminocyanine Dyes with Polyamide Dendrons: A Promising Strategy for Imaging in the Near-Infrared Region", *Chemistry—A European Journal*, vol. 17, No. 13, 2011, pp. 3619-3629.
Patolsky, Fernando et al., "Lighting up the dynamics of telomerization and DNA replication by CdSe—ZnS Quantum Dots", *J. Am. Chem. Soc.*, vol. 125, No. 46, 2003, 13918-13919.
PCT/US10/23793, , "International Search Report and Written Opinion Mailed—Nov. 11, 2010", 12.
Peng, Xiaojun et al., "Heptamethine Cyanine Dyes with a Large Stokes Shift and Strong Fluorescence: A Paradigm for Excited-State Intramolecular ChargeTransfer", *J. Am. Chem. Soc*; vol. 127, 2005,, 4170-4171.
Pham, Wellington et al., "A near-infrared dye for multichannel imaging", *Chem. Commun.*, 2008, 1895-1897.
Piston, David W. et al., "Fluorescent protein FRET: the good, the bad and the ugly", *Trends Biochem. Sci.*, vol. 32, No. 9, 2007, 407-414.

(Continued)

*Primary Examiner* — Nyeemah A Grazier

(57) ABSTRACT

Provided herein are heptamethine cyanine dyes having a large Stokes shift, and the salts and conjugates thereof. Also provided are methods of using and making such large Stokes shift dyes as fluorescence resonance energy transfer (FRET) acceptors or donors.

17 Claims, 6 Drawing Sheets

(56) References Cited

OTHER PUBLICATIONS

Strekowski, L. et al., "Substitution reactions of a nucleofugal group in heptamethine cyanine dyes. Synthesis of an isothiocyanato derivative for labeling of proteins with a near-infrared chromosphere", *J. Org. Chem.*, 57 (17), 1992, 4578-4580.

Tang, et al., *Huaxue Xuebao*, vol. 65 (13), 2005, pp. 1229-1233.

Tang, B. et al., "A Near-Infrared Neutral pH Fluorescent Probe for Monitoring Minor pH Changes: Imaging in Living HepG2 and HL-7702 Cells", *J. Am. Chem. Soc.*, 131, 2009, pp. 3016-3023.

Tang, B. et al., "A Sensitive and Selective Near-Infrared Fluorescent Probe for Mercuric Ions and Its Biological Imaging Applications", *Chem Bio Chem*, 2008, pp. 1159-1164.

Tang, B. et al., "Highly sensitive and selective near-infrared fluorescent probe for zinc and its application to macrophage cells", *Chem. Commun.*, 2006.

Willard, Dale M. et al., "CdSe—ZnS Quantum Dots as Resonance Energy Transfer Donors in a Model Protein-Protein Binding Assay", *Nano Letters*, vol. 1, No. 9, 2001, 469-474.

Zhang, Chun-Yang et al., "Single-quantum-dot-based DNA nanosensor", *Nature Materials*, vol. 4, 2005, 826-831.

LARGE STOKES SHIFT DYES

RELATED APPLICATIONS

This application is a Continuation of Ser. No. 13/148,913, filed Aug. 10, 2011, which is a U.S. National Stage Application of PCT application no. PCT/US10/23793, filed Feb. 10, 2010, which claims priority to U.S. Provisional Application No. 61/151,757, filed Feb. 11, 2009, which disclosures are herein incorporated by reference in their entirety.

TECHNICAL FIELD

The disclosure relates to fluorescent dye molecules. More particularly, described herein are fluorescent heptamethine cyanine dyes having a long Stokes shift and the uses of such dyes in fluorescence resonance energy transfer (FRET), multicolor imaging, flow cytometry, and biomolecule labeling.

BACKGROUND ART

Heptamethine cyanine dyes have attracted considerable interest because of their ability to fluoresce in the near infrared (NIR) region. However, the utility of such dyes in bioassays and in vivo applications has been limited because many dyes of this class exhibit photo-instability, poor water solubility, and a relatively small Stokes shift, typically less than about 25 nm. The Stokes shift is the difference (in wavelength or frequency units) between the peak absorption and emission spectra for the same electronic transition. Dyes having a small Stoke shifts frequently lack sensitivity due to self-quenching and interference by excitation and scattered light.

Recently, there have been reports of heptamethine cyanine dyes that exhibit increased Stokes shift propoerties. For example, Pham et al. described the preparation and properties of a near infrared dye, 4-sulfonir, having a large Stokes shift. See Pham et al., *Chem. Commun.* (2008), 1895-97. Other enamine-containing dyes have been disclosed by Peng et al. to have a large Stokes shift and strong fluorescence. See Peng et al., *J. Am. Chem. Soc.* (2005), 127:4170-71. Related dyes and dye conjugates have been reported by Wang et al. as diagnostic contrast agents. See Wang et al., U.S. Publication No. 20080206886 (published Aug. 28, 2008).

In spite of these advances, there remains a need to identify heptamethine cyanine dyes that are both photostable and chemically stable, and have an increased Stokes shifts, as well as a high quantum yield and molar extinction coefficient. Dyes exhibiting good water solubility suitable for use in bioassays are particularly desirable.

SUMMARY

Provided herein are heptamethine cyanine dyes, and the salts and conjugates thereof, having a large Stokes shift (i.e., the difference between the wavelength at which the dye has maximum absorbance and the wavelength at which the dye has maximum emission), that allows the fluorescent emission to be readily distinguished from the light source used to excite the dye. Such large Stokes shift (LSS) dyes preferably have a high quantum yield and a large extinction coefficient. This disclosure also relates to using LSS dyes in biomolecule labeling and methods of using LSS dyes as fluorescence resonance energy transfer (FRET) acceptors or donors.

In one aspect, a compound of Formula I or II is provided:

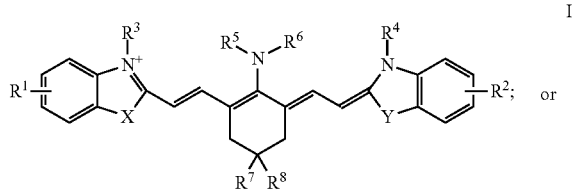

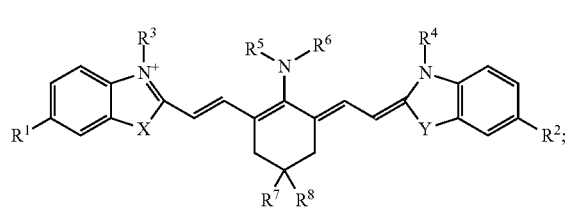

or a salt or conjugate thereof;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_m SO_3H$, $(CH_2)_n$ COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can independently be a H, $C_{1-6}$ carbonyl, or $C_{1-6}$ alkyl which can be optionally substituted one or more times by an amino, maleimide, thiol, isocyanate, isothiocyanate, disulfide, alkynyl, azidoyl or trialkoxysilane;

$R^7$ and $R^8$ can independently be H, $C_{1-4}$ alkyl, or phenyl;

X and Y can independently be $CR^9_2$, $NR^{10}$, O, S, or Se; and each of $R^9$ and $R^{10}$ can independently be $C_{1-4}$ alkyl.

In another aspect, a compound of Formula I or II, is provided:

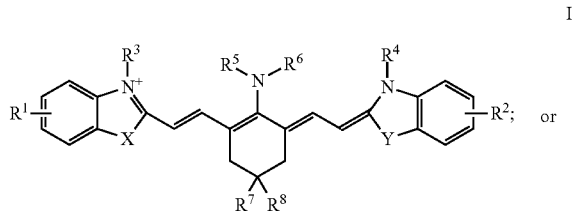

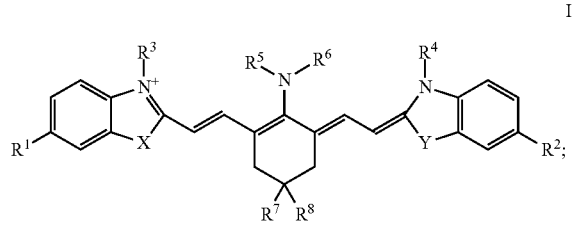

or a salt or conjugate thereof;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_m SO_3H$, $(CH_2)_n$ COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can be taken together with the nitrogen atom to which they are attached to form an optionally substituted 5- or 6-membered azacyclic ring, optionally containing an additional heteroatom selected from N, O and S as a ring member;

$R^7$ and $R^8$ can independently be H, $C_{1-4}$ alkyl, or phenyl;

X and Y can independently be $CR^9_2$, $NR^{10}$, O, S or Se; and each $R^9$ and $R^{10}$ can independently be $C_{1-4}$ alkyl.

In a further aspect, a compound of Formula III, is provided:

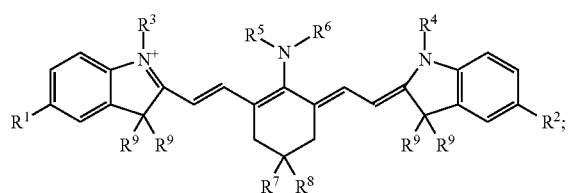

(III)

or a salt or conjugate thereof;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_mSO_3H$, $(CH_2)_n$COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can independently be a H, $C_{1-6}$ carbonyl, or $C_{1-6}$ alkyl which can be optionally substituted one or more times by an amino, maleimide, thiol, isocyanate, isothiocyanate, disulfide, alkynyl, azidoyl or trialkoxysilane;

$R^7$ and $R^8$ can independently be H, $C_{1-4}$ alkyl, or phenyl; and each $R^9$ can independently be $C_{1-4}$ alkyl.

In another aspect, a compound of Formula III, is provided:

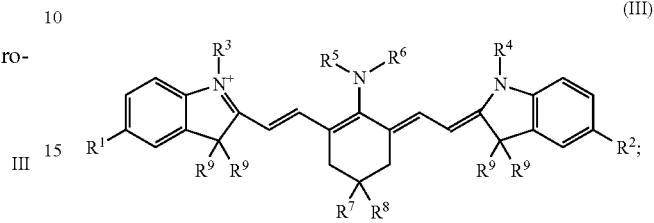

(III)

or a salt or conjugate thereof;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_mSO_3H$, $(CH_2)_n$COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ cab be taken together with the nitrogen atom to which they are attached to form an optionally substituted 5- or 6-membered azacyclic ring, optionally containing an additional heteroatom selected from N, O and S as a ring member;

$R^7$ and $R^8$ can independently be H, $C_{1-4}$ alkyl, or phenyl; and each $R^9$ can independently be $C_{1-4}$ alkyl.

In yet another aspect, a compound selected from:

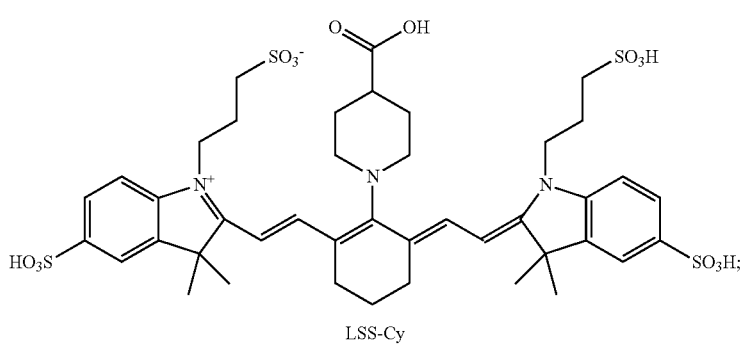

LSS-Cy

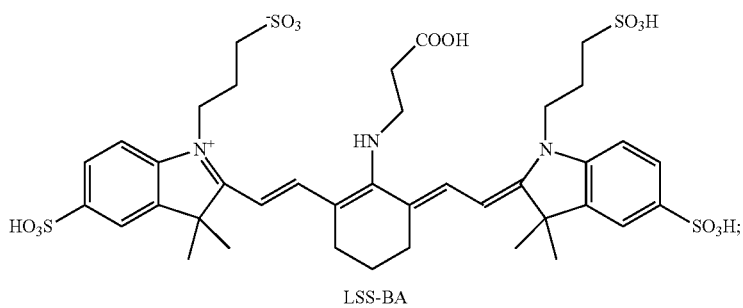

LSS-BA

-continued
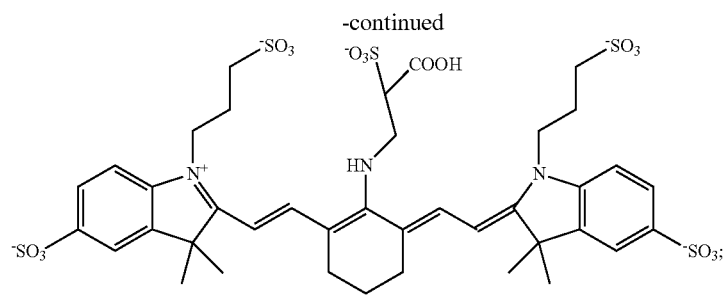
LSS-BAS
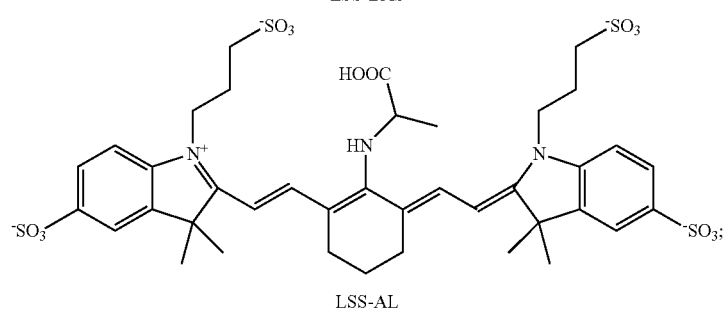
LSS-AL
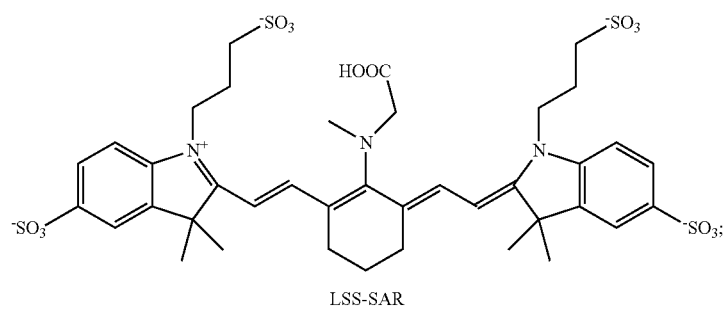
LSS-SAR
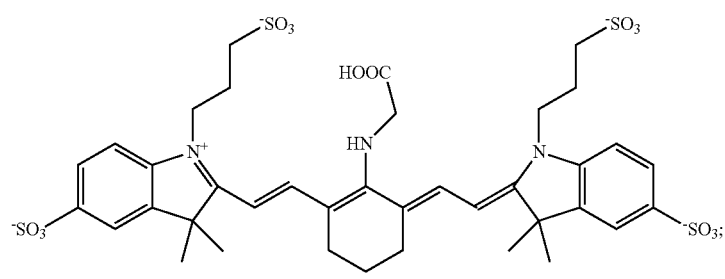
LSS-GL
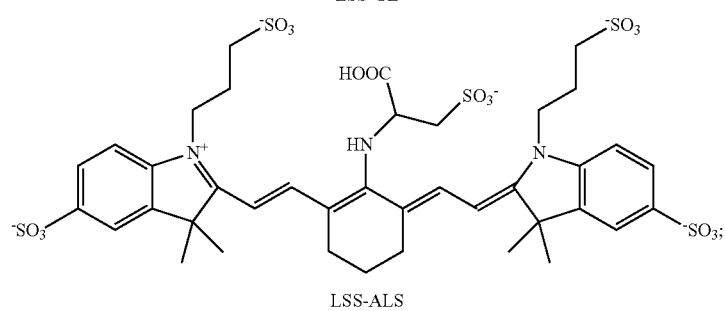
LSS-ALS -continued
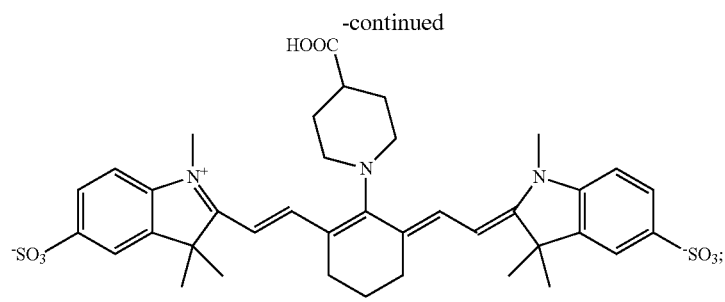
LSS-CY LITE
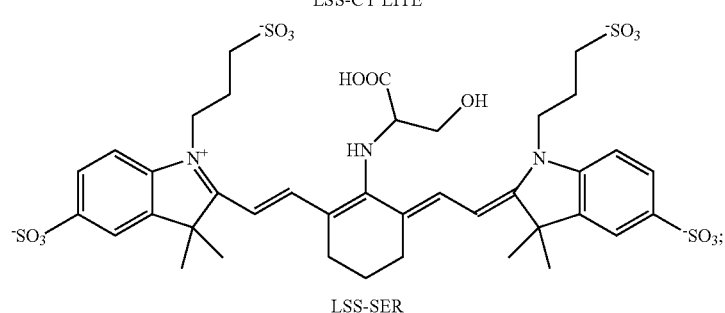
LSS-SER
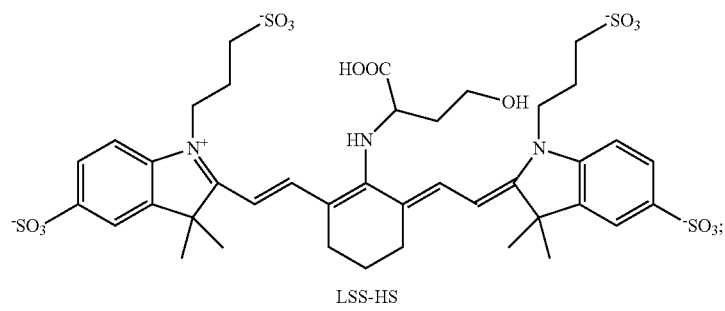
LSS-HS
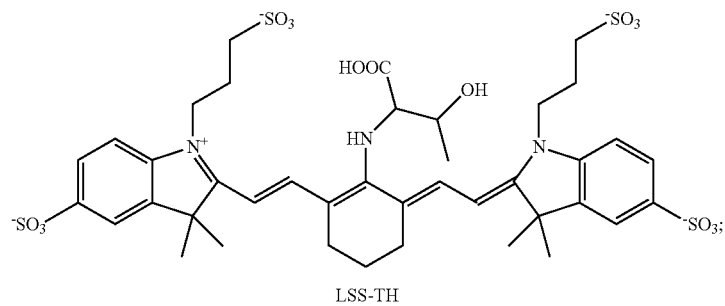
LSS-TH
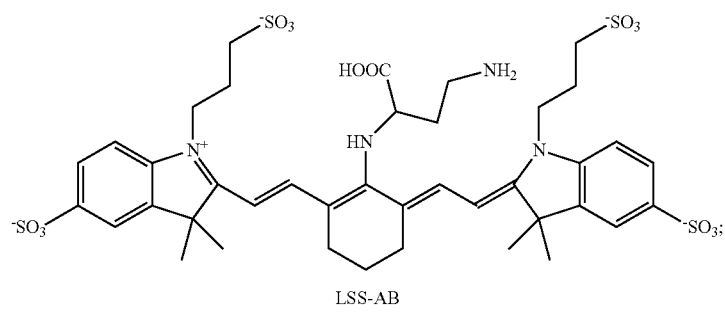
LSS-AB -continued
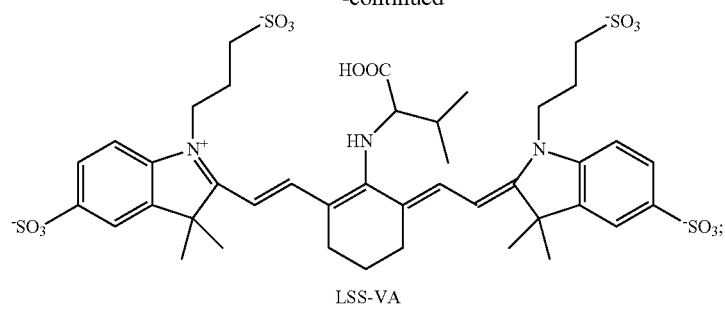
LSS-VA
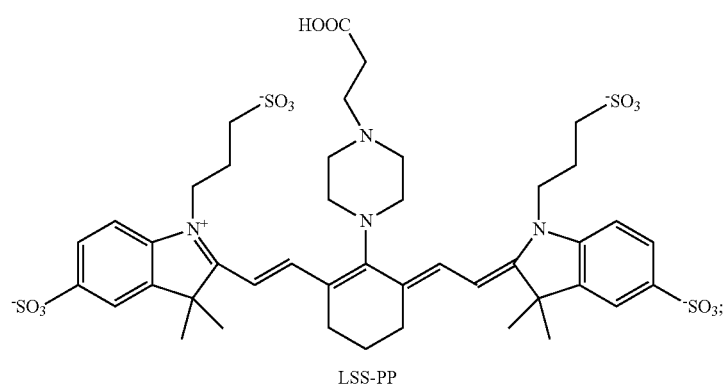
LSS-PP
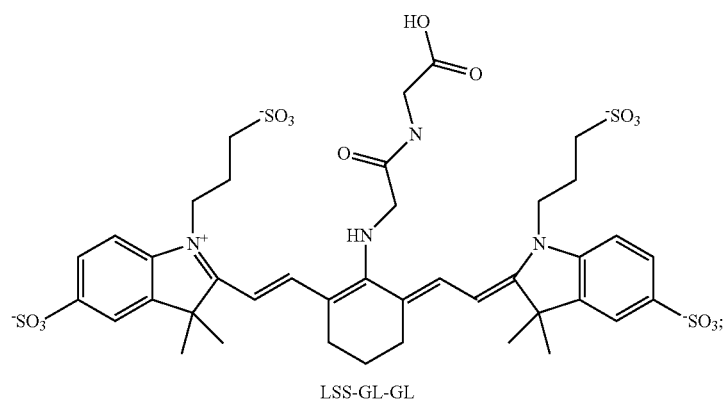
LSS-GL-GL
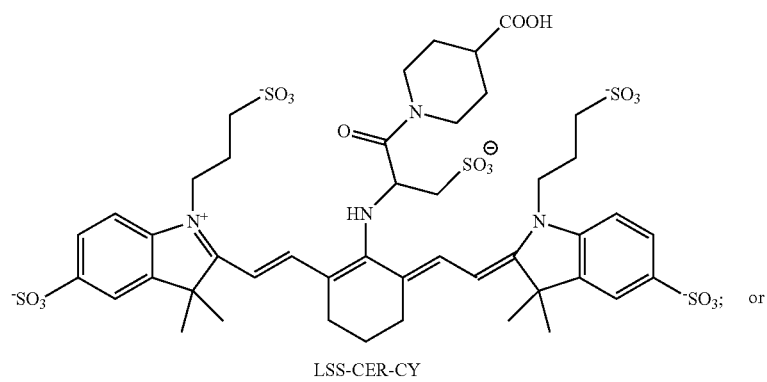
LSS-CER-CY; or

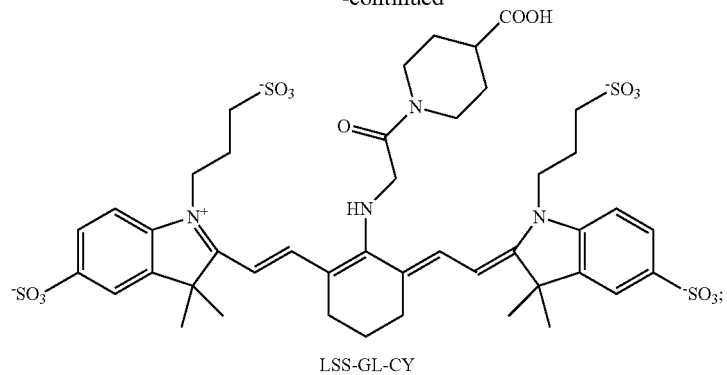

LSS-GL-CY or a salt or conjugate thereof, is provided.

In another aspect, a fluorescing molecular complex, is provided, comprising:

a donor dye capable of absorbing light at a first wavelength and emitting excitation energy in response; and an acceptor dye capable of absorbing the excitation energy emitted by the donor dye and fluorescing at a second wavelength in response;

wherein either said donor dye or said acceptor dye has the structure of Formula I, II, III, IV, V, VI or VII or a salt or conjugate thereof, as further described herein.

In one embodiment, a fluorescing molecular complex, is provided, comprising:

a donor dye capable of absorbing light at a first wavelength and emitting excitation energy in response; and an acceptor dye capable of absorbing the excitation energy emitted by the donor dye and fluorescing at a second wavelength in response;

wherein either said donor dye or said acceptor dye has the structure of Formula III:

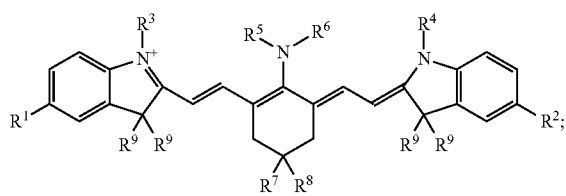

or a salt or conjugate thereof;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_m SO_3H$, $(CH_2)_n$ COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can independently be a H, $C_{1-6}$ carbonyl, or $C_{1-6}$ alkyl which can be optionally substituted one or more times by an amino, maleimide, thiol, isocyanate, isothiocyanate, disulfide, alkynyl, azidoyl or trialkoxysilane;

$R^7$ and $R^8$ can independently be H, $C_{1-4}$ alkyl, or phenyl; and each $R^9$ can independently be a $C_{1-4}$ alkyl.

In another embodiment, a fluorescing molecular complex, is provided, comprising:

a donor dye capable of absorbing light at a first wavelength and emitting excitation energy in response; and an acceptor dye capable of absorbing the excitation energy emitted by the donor dye and fluorescing at a second wavelength in response;

wherein either said donor dye or said acceptor dye has the structure of Formula III:

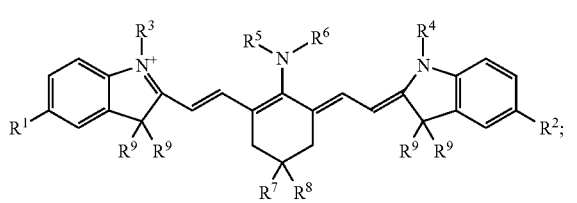

or a salt or conjugate thereof;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_m SO_3H$, $(CH_2)_n$ COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can be taken together with the nitrogen atom to which they are attached to form an optionally substituted 5- or 6-membered azacyclic ring, optionally containing an additional heteroatom selected from N, O and S as a ring member;

$R^7$ and $R^8$ can independently be H, $C_{1-4}$ alkyl, or phenyl; and each $R^9$ can independently be $C_{1-4}$ alkyl.

In further embodiments, a compound of Formula IV, V or VI:

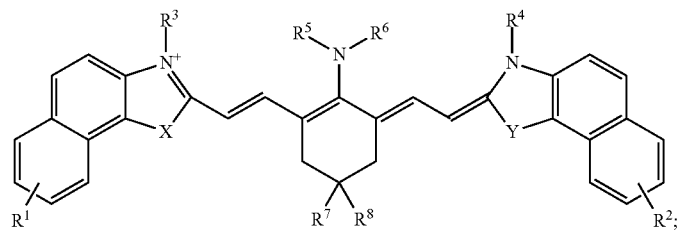

IV

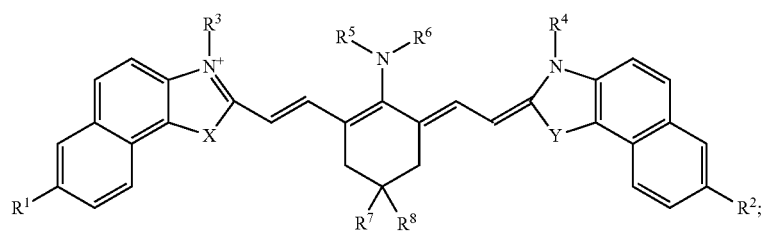

V

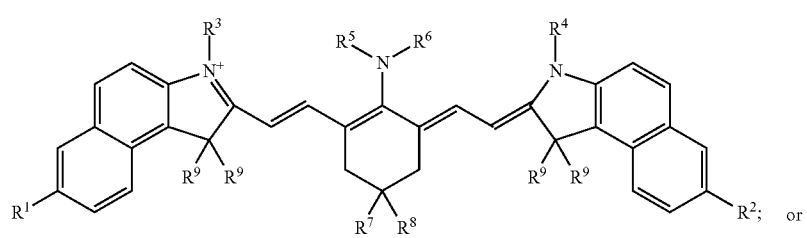

VI

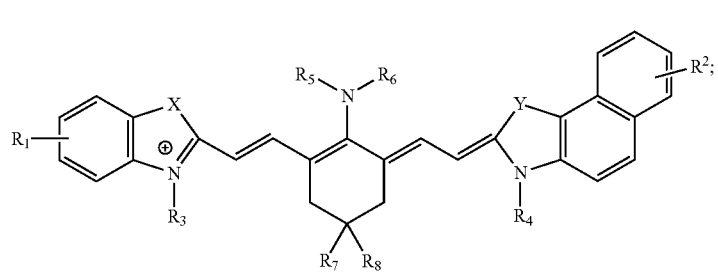

VII or a salt or conjugate thereof, is provided;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_m SO_3H$, $(CH_2)_n$ COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can independently be a H, $C_{1-6}$ carbonyl, or $C_{1-6}$ alkyl which can be optionally substituted one or more times by an amino, maleimide, thiol, isocyanate, isothiocyanate, disulfide, alkynyl, azidoyl or trialkoxysilane;

$R^7$ and $R^8$ can independently be H, $C_{1-4}$ alkyl, or phenyl;

X and Y, where present, can independently be $CR^9_2$, $NR^{10}$, O, S or Se; and each $R^9$ and $R^{10}$ can independently be $C_{1-4}$ alkyl.

In still further embodiments, a compound of Formula IV, V, VI, or VII:

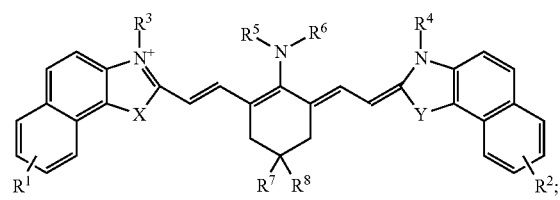

IV

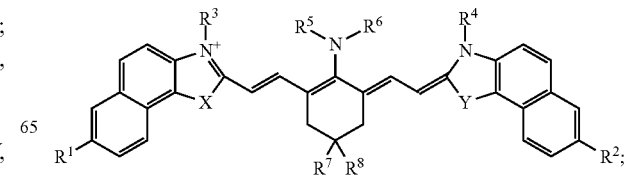

V

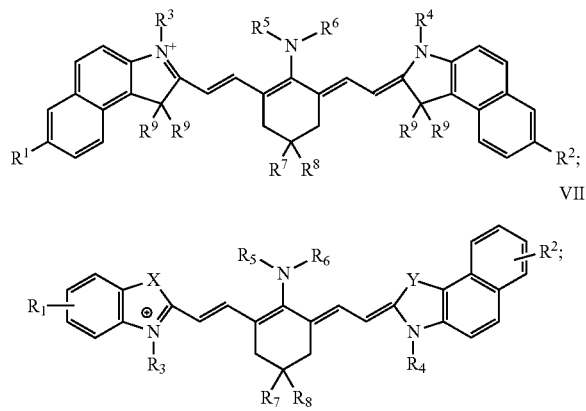

or a salt or conjugate thereof, is provided;

wherein each of $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH;

$R^3$ and $R^4$ can independently be a $(CH_2)_mSO_3H$, $(CH_2)_n$COOH or $C_{1-6}$ alkyl which can be optionally substituted one or more times by a halo, hydroxyl, $C_{1-6}$ alkyl, or amino, wherein m and n can independently be integers from 1 to 6;

$R^5$ and $R^6$ can be taken together with the nitrogen atom to which they are attached to form an optionally substituted 5- or 6-membered azacyclic ring, optionally containing an additional heteroatom selected from N, O and S as a ring member;

$R^7$ and $R^8$ can independently be H, $C_{1-4}$ alkyl, or phenyl;

X and Y, where present, can independently be $CR^9_2$, $NR^{10}$, O, S or Se; and each $R^9$ and $R^{10}$ can independently be $C_{1-4}$ alkyl.

It should be understood that compounds of Formulae I, II, III, IV, V, VI, and VII are capable of forming tautomers, and that all tautomeric forms of the compounds disclosed herein are included within the scope of what is described herein.

Compounds described herein are frequently prepared in the form of salts, and salt forms are included within the scope of those embodiments. The formation of salts, and the number and nature of counterions present, will depend on, e.g., the pH of the solution, the reagents used, and the functional groups present in the molecule.

In addition, the various embodiments of the compounds described herein may be conjugated to other moieties, including biomolecules, affinity molecules, ligands, inorganic substrates, and the like, as further described herein. Such conjugates are also included within the scope of the embodiments described herein.

The LSS dyes described herein may be used in a variety of applications, including bioassays and in vivo applications. In one aspect, the embodiments provide methods of using the compounds described herein, or salts or conjugates thereof, as FRET donors, or preferably, as FRET acceptors. In particular, certain compounds described herein absorb strongly at around 605 nm, and emit strongly around 750-800 nm, allowing them to serve as the reddest (i.e., emit at the upper wavelength range of visible light) acceptors for FRET applications.

In another aspect, methods of using the various embodiments of the compounds described herein for multicolor imaging are provided. In a further aspect, methods of using the various embodiments of the compounds described herein for flow cytometry, are further provided.

DETAILED DESCRIPTION

Figure 1:
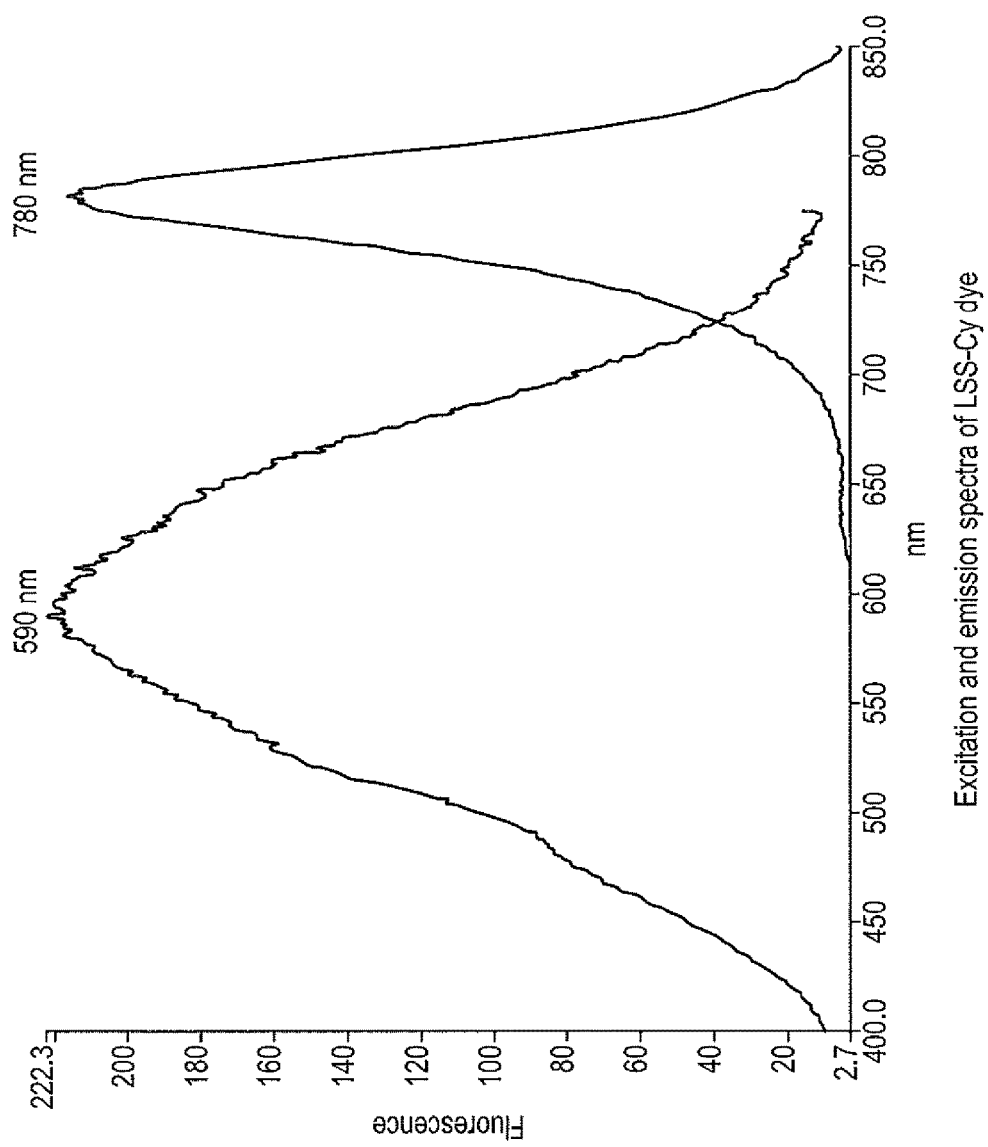
FIG. 1 shows the excitation and emission spectra of LSS-Cy dye.
Figure 2A:
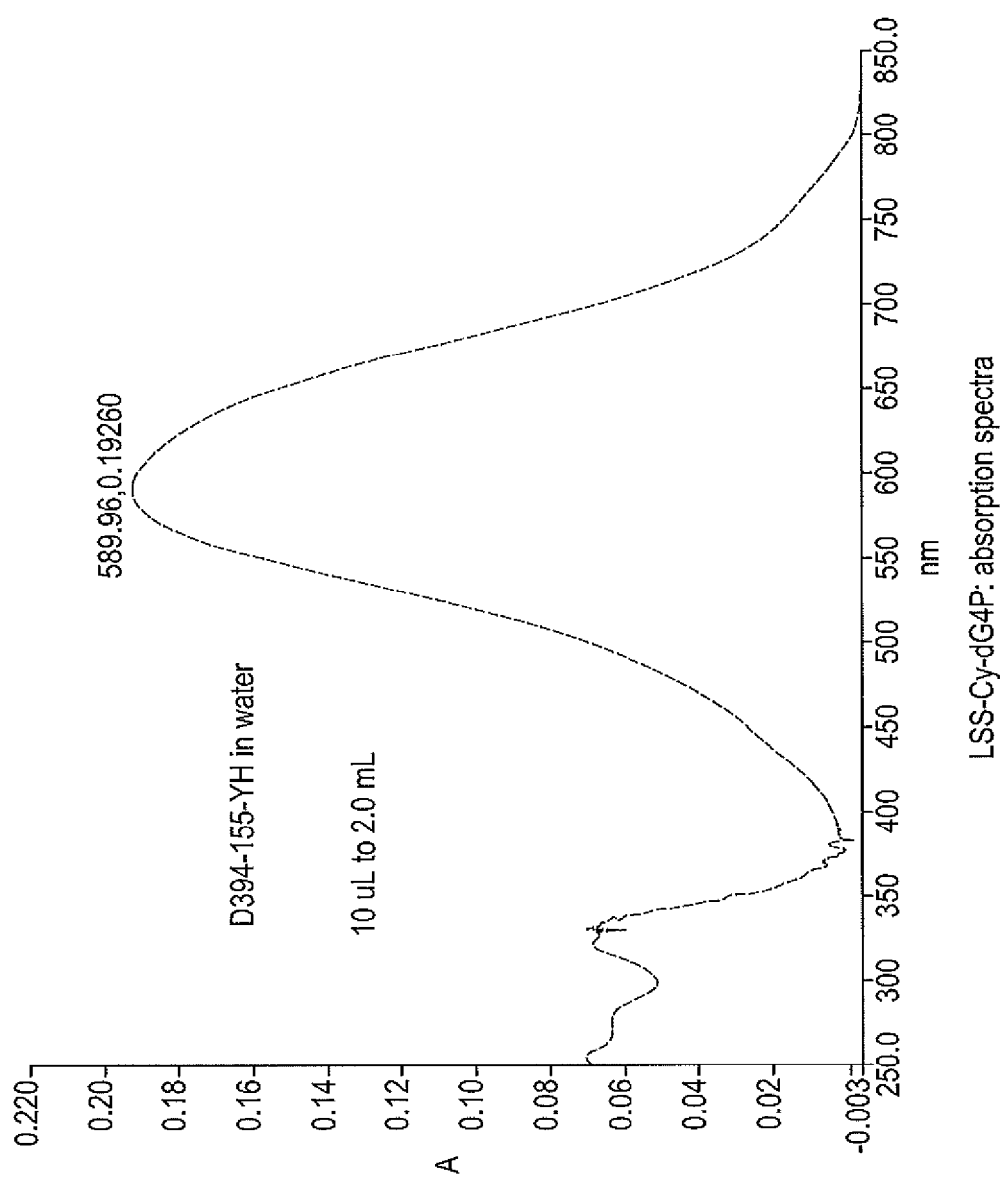
FIG. 2A shows the absorption spectra of the LSS-Cy dye deoxyguanosine tetraphosphate (dG4P) conjugate, LSS-Cy-dG4P.
Figure 2B:
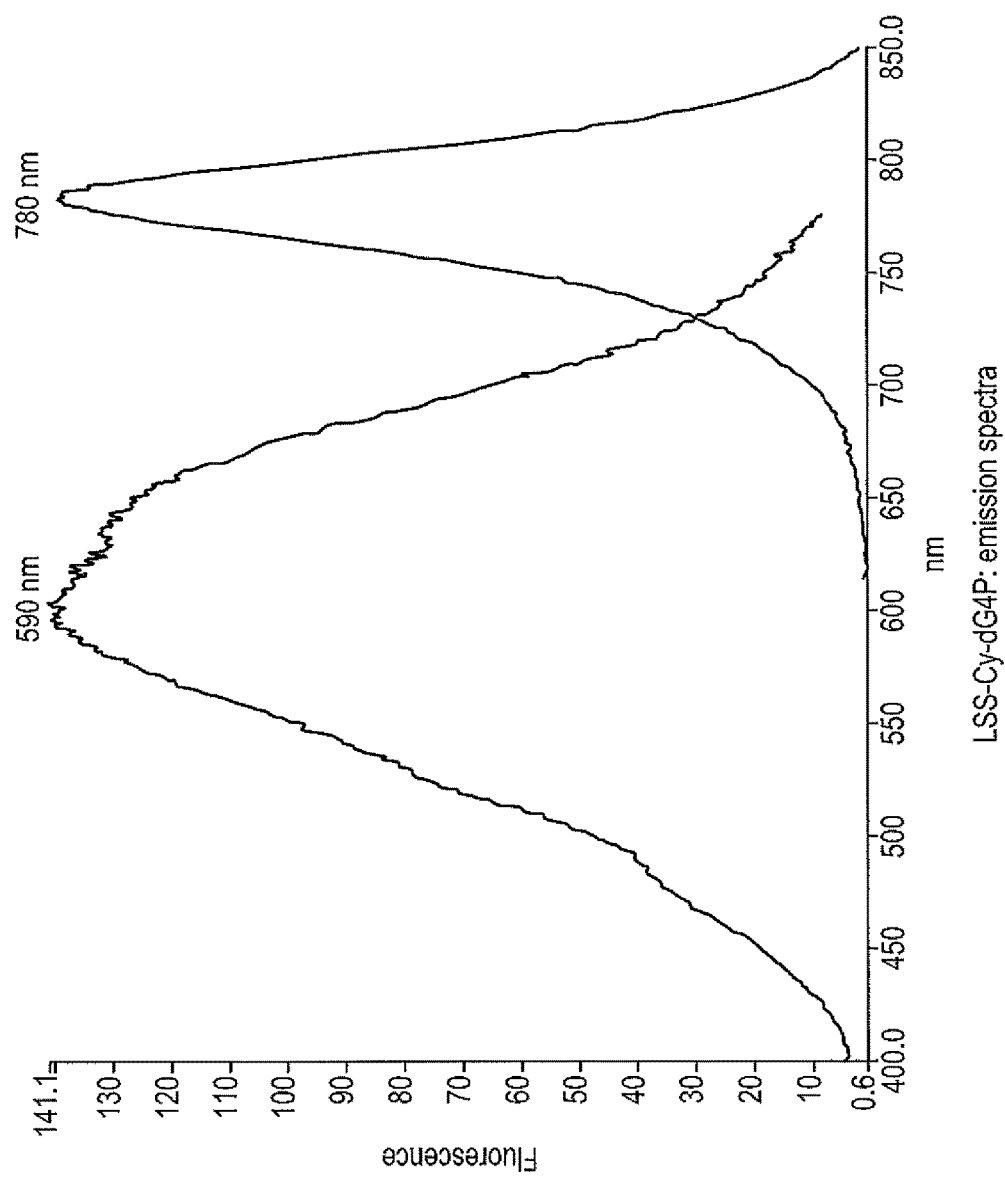
FIG. 2B shows the emission spectra of LSS-Cy-dG4P.
Figure 3:
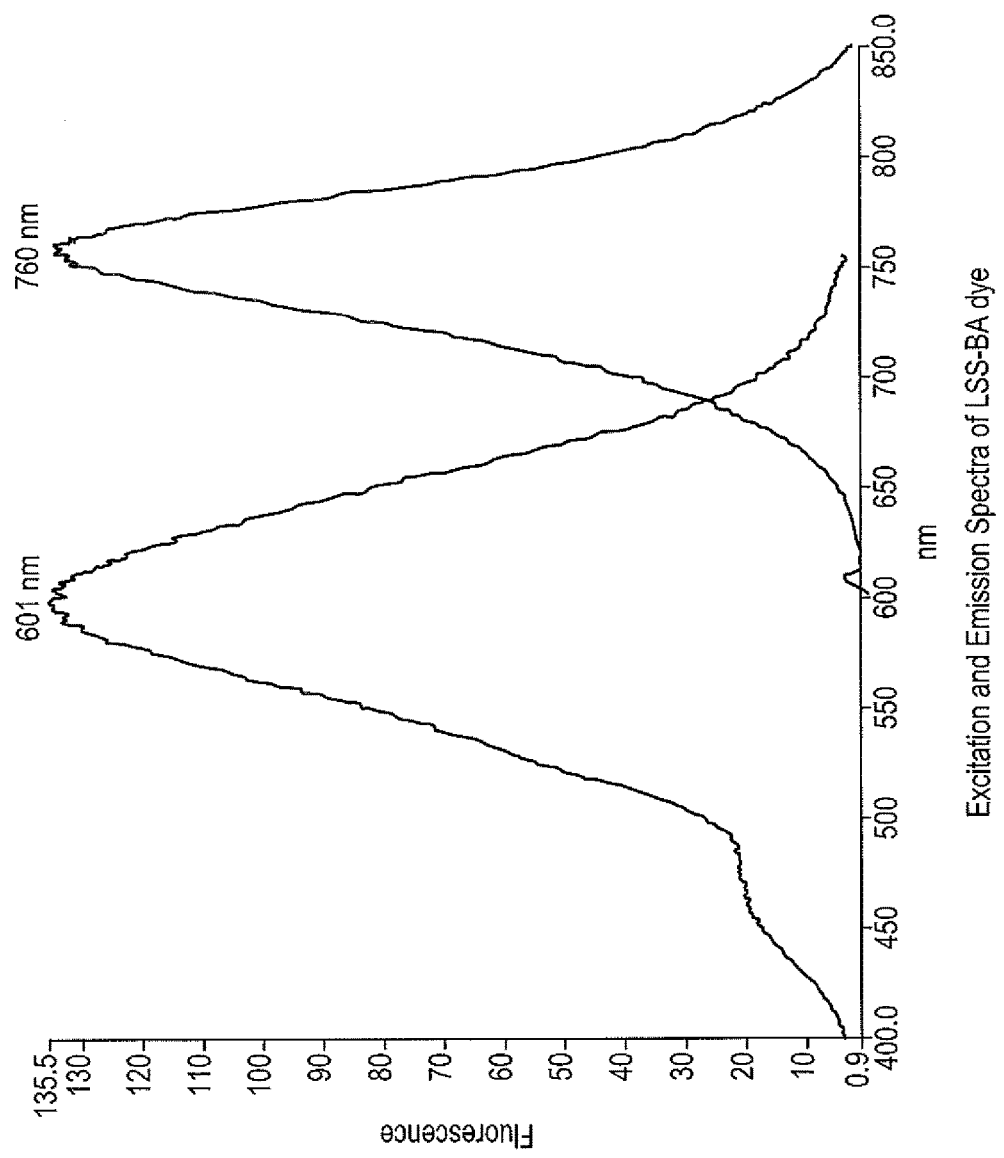
FIG. 3 shows the excitation and emission spectra of LSS-BA dye.
Figure 4A:
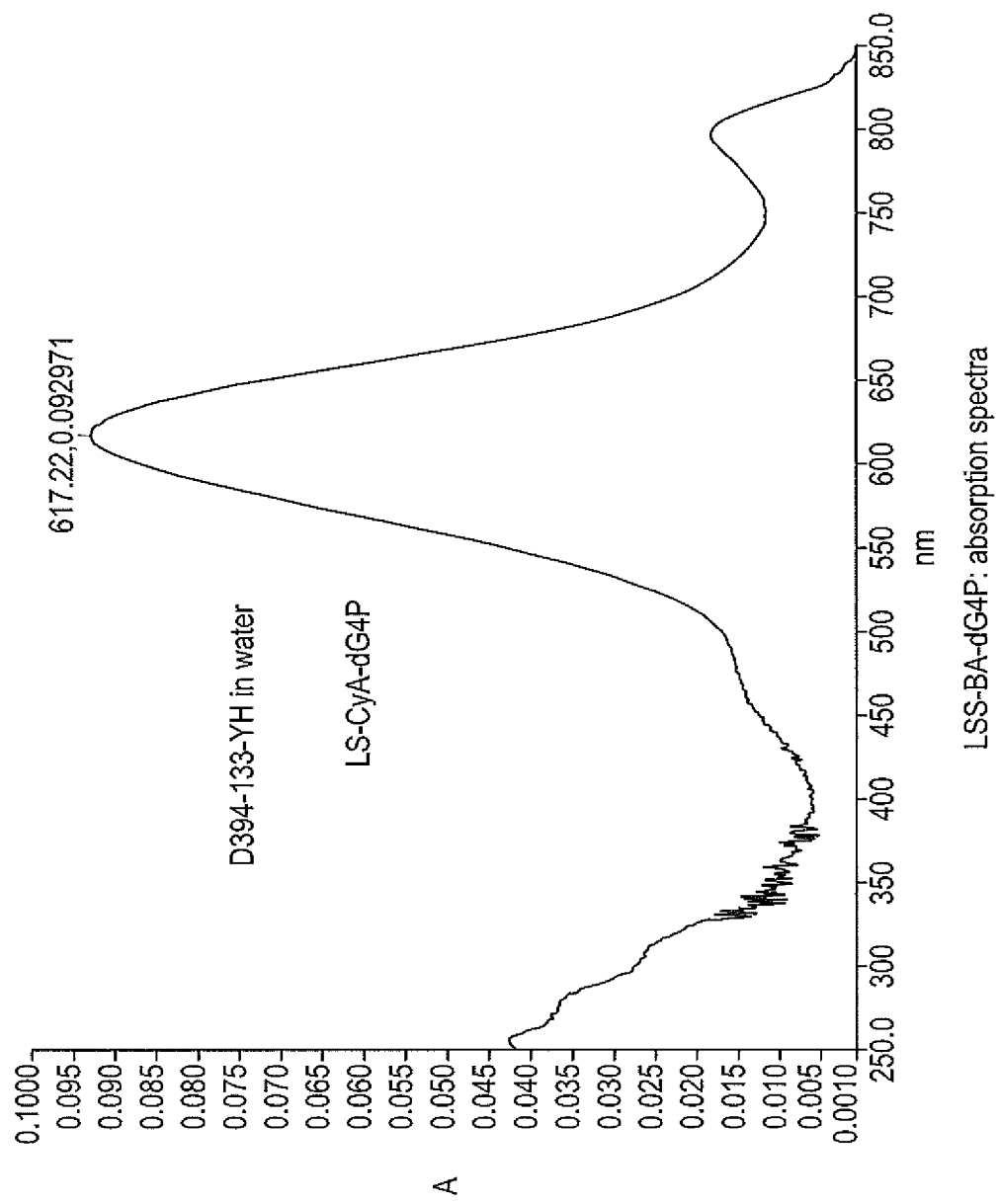
FIG. 4A shows the absorption spectra of the LSS-BA dye dG4P conjugate, LSS-BA-dG4P.
Figure 4B:
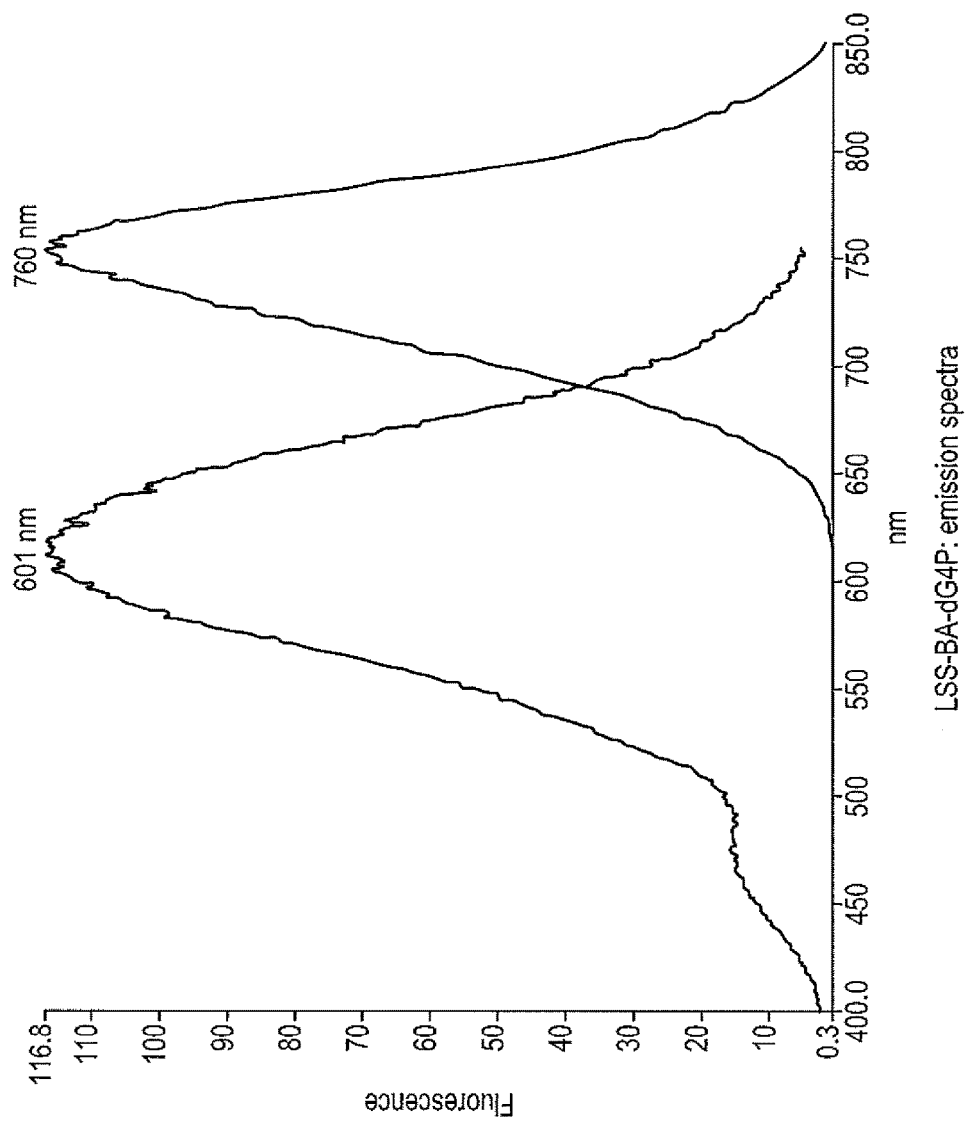
FIG. 4B shows the emission spectra of LSS-BA-dG4P.

The embodiments described herein may be understood more readily by reference to the following detailed description of the embodiments and the Examples included herein. It should be understood that the terminology used herein is for the purpose of describing specific embodiments only and is not intended to be limiting. Furthermore, in the following detailed description of the embodiments, numerous specific details are set forth in order to provide a thorough understanding of them.

Unless defined otherwise, all technical and scientific terms used herein have the same meaning as is commonly understood by one of ordinary skill in the art.

As used herein, "a" or "an" means "at least one" or "one or more."

"Optional" or "optionally" means that the subsequently described event or circumstance may or may not occur, and that the description includes instances where the event occurs and instances where it does not.

As used herein, "about" means that the numerical value is approximate and small variations would not significantly affect the practice of the embodiments described herein and remain within the scope of the embodiments. Where a numerical limitation is used, unless indicated otherwise by the context, "about" means the numerical value can vary by ±10% and remain within the scope of the embodiments.

As used herein, "water soluble" means the item is soluble or suspendable in an aqueous-based solution, such as in water or water-based solutions or buffer solutions, including those used in biological or molecular detection systems as known by those skilled in the art.

The Stokes shift of a dye refers to the difference between the wavelength at which the dye has maximum absorbance and the wavelength at which the dye has maximum emission. As used to herein, a "large Stokes shift" (LSS) dye refers to a dye in which the Stokes shift is greater than about 30 nm, sometimes greater than about 50 nm, and preferably greater than about 70 nm. The various embodiments of the compounds described herein typically have a Stokes shift ranging from about 30 nm to about 250 nm, sometimes from about 50 nm to about 225 nm, preferably from about 70 nm to about 200 nm.

Moreover, it should be appreciated that any of the compounds described herein can be part of a substantially pure compound composition typically containing between about 70% to about 100% of a particular compound, sometimes containing between about 80% to about 95% of a particular compound, preferably containing between about 90% to about 95% of a particular compound.

The terms "molar extinction coefficient" or "molar absorptivity" (i.e., epsilon, e, in units of $M^{-1}cm^{-1}$) relate to the absorption efficiency, or how strongly a substance absorbs light at a given wavelength per molar concentration.

The quantum yield of a radiation-induced process is the number of times that a defined event, such as emission, occurs per photon absorbed. As used herein, the term "quantum yield" is a measure of the emission efficiency.

As used herein, the terms "alkyl," "alkenyl" and "alkynyl" include straight-chain, branched-chain and cyclic monovalent hydrocarbyl radicals, and combinations thereof, which contain only C and H when they are unsubstituted. Examples include, but are not limited to, methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as $C_1$-$C_{10}$ or as $C_{1-10}$. When heteroatoms (such as N, O and S) are allowed to replace carbon atoms of an alkyl, alkenyl or alkynyl group, as in heteroalkyl groups, for example, the numbers describing the group, though still written as e.g. $C_1$-$C_6$, represent the sum of the number of carbon atoms in the group plus the number of such heteroatoms that are included as replacements for carbon atoms in the ring or chain being described.

Typically, the alkyl, alkenyl and alkynyl substituents of the embodiments described herein contain, but are not limited to, 1-10C (alkyl) or 2-10C (alkenyl or alkynyl). Sometimes they contain 1-8C (alkyl) or 2-8C (alkenyl or alkynyl). Preferably, they contain 1-6C (alkyl) or 2-6C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

Alkyl, alkenyl and alkynyl groups are often substituted to the extent that such substitution can chemically occur. Typical examples of substituents can include, but are not limited to, halo, acyl, heteroacyl, carboxylic acid, sulfonic acid, primary or secondary amine, thiol, hydroxyl, or an activated derivative thereof, or a protected form of one of these. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group.

As used herein, "acyl" encompasses groups comprising an alkyl, alkenyl, alkynyl, aryl or arylalkyl radical attached at one of the two available valence positions of a carbonyl carbon atom, e.g., —C(=O)R where R can be an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)-heteroaryl, where each R is independently H, or C1-C8 alkyl.

"Aromatic" moiety or "aryl" moiety refers to a monocyclic or fused bicyclic moiety having the well-known characteristics of aromaticity; examples include, but are not limited to, phenyl and naphthyl. Similarly, "heteroaromatic" and "heteroaryl" refer to such monocyclic or fused bicyclic ring systems which contain as ring members one or more heteroatoms (such as O, S and N). The inclusion of a heteroatom permits aromaticity in 5-membered rings as well as 6-membered rings. Typical heteroaromatic systems include, but are not limited to, monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Preferably aryl groups contain 6-10 ring members, and heteroaryl groups contain 5-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties can include halo, OR, $NR_2$, SR, $SO_2R$, $SO_2NR_2$, $NRSO_2R$, $NRCONR_2$, NRCOOR, NRCOR, CN, COOR, $CONR_2$, OOCR, —C(O)R, and $NO_2$, wherein each R is independently H, or C1-C8 alkyl.

In one aspect, a compound of Formula I or II:

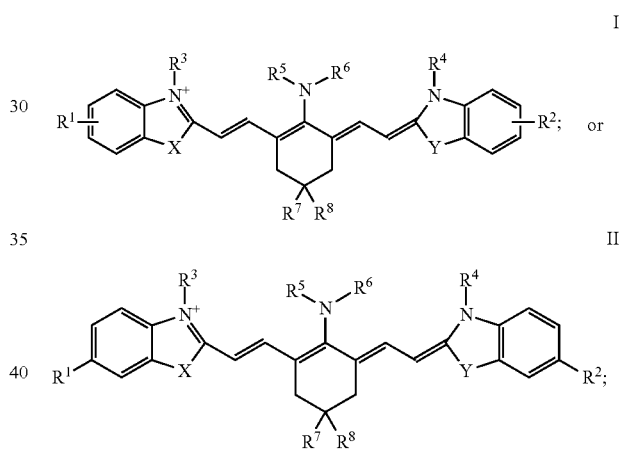

or a salt or conjugate thereof, is provided.

In compounds of Formula I and Formula II, $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH. In some embodiments, $R^1$ and $R^2$ are different. In other embodiments, $R^1$ and $R^2$ are the same. In some such embodiments, each of $R^1$ and $R^2$ is $SO_3H$.

In compounds of Formula I and Formula II, $R^3$ and $R^4$ can independently be a $(CH_2)_m SO_3H$, $(CH_2)_n COOH$ or $C_{1-6}$ alkyl (which can be optionally substituted one or more times by a halo, hydroxyl, $C_{1-6}$ alkyl, or amino), wherein m and n are independently integers from 1 to 6. In certain embodiments, each of m and n is an integer from 2 to 4. In some embodiments, $R^3$ and $R^4$ are different. In other embodiments, $R^3$ and $R^4$ are the same. In certain embodiments, each of $R^3$ and $R^4$ is $(CH_2)_m SO_3H$. In some such embodiments, m is an integer from 2 to 4; in specific embodiments, m is 3.

In some embodiments of Formula I and Formula II, $R^5$ and $R^6$ can independently be H, $C_{1-6}$ carbonyl, or optionally substituted $C_{1-6}$ alkyl.

Optional substituents when present on the $C_{1-6}$ alkyl groups at $R^5$ and $R^6$ include for example, halo, acyl, heteroacyl, carboxylic acid, primary or secondary amine, thiol, hydroxyl, maleimide, isocyanate, isothiocyanate, disulfide, alkynyl, azidoyl, trialkoxysilane, or an activated derivative thereof. Activated derivatives of carboxylic acids can include, e.g., activated esters, such as N-hydroxysuccinimide (NHS) esters, hydroxybenzotriazole (HOBT) or 1-hydroxy-7-aza-benzotriazole (HOAt) esters, or mixed anhydrides. Activated amines can include, e.g., N-acyl imidazolides, while activated thiols and hydroxyls can include, e.g., imidazole carbamate and thiocarbamate derivatives, and succinimidyl carbonates and thiocarbonate derivatives, and sulfonate esters and thioesters. Other suitable activated derivatives are known to those of skill in the art.

In other embodiments of Formula I and Formula II, $R^5$ and $R^6$ are taken together with the nitrogen atom to which they are attached to form an optionally substituted 5- or 6-membered azacyclic ring substituted, optionally containing an additional heteroatom selected from N, O and S as a ring member.

Optional substituents when present on the azacyclic ring formed by $R^5$ and $R^6$ can include, for example, halo, acyl, heteroacyl, carboxylic acid, primary or secondary amine, thiol, hydroxyl, or $C_{1-6}$ alkyl substituted with halo, acyl, heteroacyl, carboxylic acid, primary or secondary amine, thiol, or hydroxyl, or an activated derivative of any of the above, where activated derivatives for various functional groups are the same as those provided above for substituents on $C_{1-6}$ alkyl groups at $R^5$ and $R^6$.

In compounds of Formula I and Formula II, $R^7$ and $R^8$ can independently be H, $C_{1-4}$ alkyl, or phenyl. In some embodiments, each of $R^7$ and $R^8$ is H. In other embodiments, one of $R^7$ and $R^8$ is H and the other is phenyl or tert-butyl.

In compounds of Formula I and Formula II, X and Y can independently be $CR^9_2$, $NR^{10}$, O, S, or Se; where each of $R^9$ and $R^{10}$ is independently $C_{1-4}$ alkyl. In certain embodiments, each $R^9$ and $R^{10}$ are preferably methyl.

In some embodiments of Formula I and Formula II, X and Y are different. In other embodiments, X and Y are the same. In specific embodiments, each of X and Y is $CR^9_2$, where each $R^9$ is independently $C_{1-4}$ alkyl. In some such embodiments, each $R^9$ is methyl.

In certain preferred embodiments of Formula I and Formula II, $R^1$ and $R^2$ are the same, $R^3$ and $R^4$ are the same, and X and Y are the same.

In another aspect, compound of Formula III:

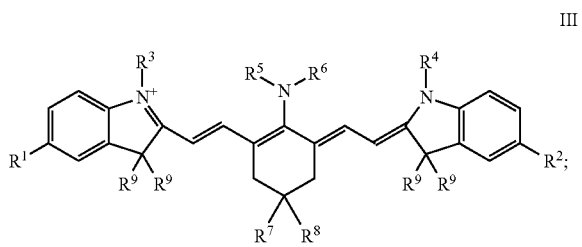

III or a salt or conjugate thereof, is provided.

In compounds of Formula III, $R^1$ and $R^2$ can independently be H, halo, hydroxyl, amino, $C_{1-6}$ alkylamino, $C_{2-12}$ dialkylamino, $C_{1-6}$ perfluoroalkyl, $C_{1-6}$ alkyl, $C_{1-6}$ alkoxy, $SO_3H$ or COOH. In some embodiments, $R^1$ and $R^2$ are different. In other embodiments, $R^1$ and $R^2$ are the same. In some such embodiments, each of $R^1$ and $R^2$ is $SO_3H$.

In compounds of Formula III, $R^3$ and $R^4$ can independently be a $(CH_2)_mSO_3H$, $(CH_2)_nCOOH$ or $C_{1-6}$ alkyl (which can be optionally substituted one or more times by a halo, hydroxyl, $C_{1-6}$ alkyl, or amino), wherein m and n are independently integers from 1 to 6. In certain embodiments, each of m and n is an integer from 2 to 4. In some embodiments, $R^3$ and $R^4$ are different. In other embodiments, $R^3$ and $R^4$ are the same. In certain embodiments, each of $R^3$ and $R^4$ is $(CH_2)_mSO_3H$. In some such embodiments, m is an integer from 2 to 4; in specific embodiments, m is 3.

In some embodiments of Formula III, $R^5$ can be H, or optionally substituted $C_{1-6}$ alkyl; and $R^6$ can be $C_{1-6}$ carbonyl, or optionally substituted $C_{1-6}$ alkyl. In other embodiments of Formula III, $R^5$ and $R^6$ can be taken together with the nitrogen atom to which they are attached to form an optionally substituted 5- or 6-membered azacyclic ring substituted, optionally containing an additional heteroatom selected from N, O and S as a ring member.

Optional substituents when present on $R^5$, $R^6$, or on the azacyclic ring formed by $R^5$ and $R^6$, are the same as those provided herein for compounds Formula I and Formula II.

In compounds of Formula III, $R^7$ and $R^8$ can independently be H, $C_{1-4}$ alkyl, or phenyl. In some embodiments, each of $R^7$ and $R^8$ is H. In other embodiments, one of $R^7$ and $R^8$ is H and the other is phenyl or tert-butyl.

In compounds of Formula III, each $R^9$ can independently be $C_{1-4}$ alkyl. In certain embodiments, each $R^9$ is the same; preferably, each $R^9$ is methyl.

In certain preferred embodiments of Formula III, $R^1$ and $R^2$ are the same, $R^3$ and $R^4$ are the same, and each $R^9$ is the same. In some such embodiments, each of $R^7$ and $R^8$ is H.

In further embodiments, a compound of Formula IV, V, VI, or VII:

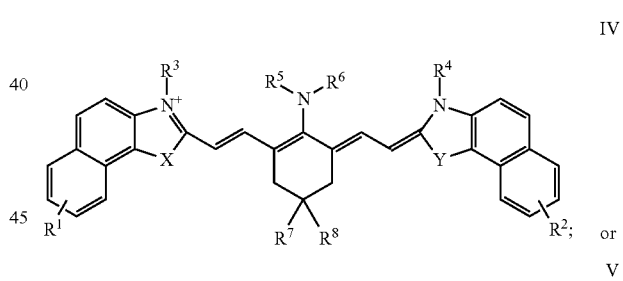

IV or

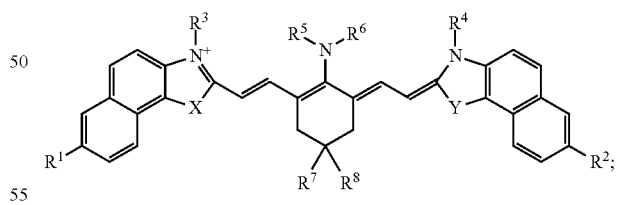

V

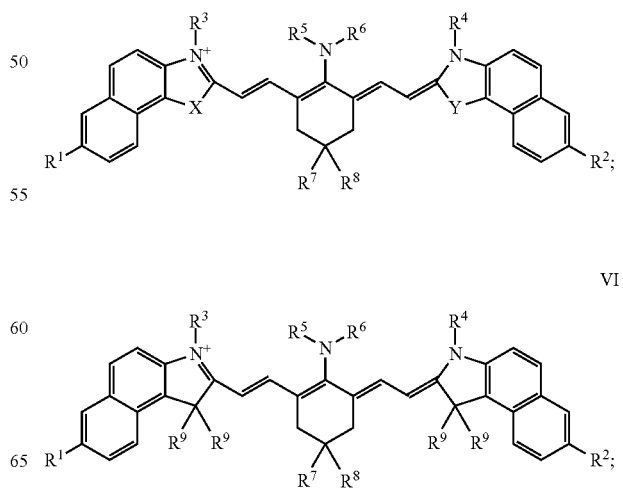

VI

VII

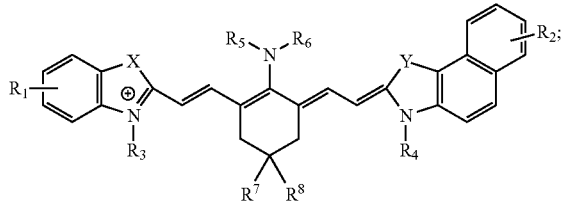

or a salt or conjugate thereof, is provided.

The same groups described herein for X, Y, $R^1$, $R^2$, $R^3$, $R^4$, $R^5$, $R^6$, $R^7$, $R^8$, $R^9$, and $R^{10}$ for compounds of Formula I, II and III are also useful for compounds of Formula IV, V, VI and VII.

The compounds described above, or the salts and conjugates thereof, have a large Stokes shift which is greater than about 30 nm, sometimes greater than about 50 nm, and preferably greater than about 70 nm. In some embodiments, the compounds, salts and conjugates thereof have a Stokes shift from about 30 nm to about 250 nm. In other embodiments, the Stokes shift is from about 50 nm to about 225 nm. Preferably, the Stokes shift is from about 70 nm to about 200 nm.

Without wishing to be bound by theory, it is believed that the presence of the enamine functionality on the central cyclohexenyl ring contributes significantly to the absorption and emission spectra of the embodiments of the dyes described herein. The enamine nitrogen atom is substituted with the groups $R^5$ and $R^6$, which can be substituted with a functional group suitable for conjugation to another moiety, as further described herein.

The compounds described herein, or the salts or conjugates thereof, are typically soluble in water or aqueous solutions or buffers typically used in biological systems and assays.

The compounds described herein are particularly useful in applications related to fluorescence resonance energy transfer (FRET). FRET is a distance-dependent interaction between the electronic excited states of two dye molecules in which excitation energy is transferred from a donor molecule to an acceptor molecule. The efficiency of FRET is dependent on the inverse sixth power of the separation distance between the donor molecule and acceptor molecule (i.e., intermolecular separation), making it useful over distances comparable with the dimensions of biological macromolecules. Thus, FRET is an important technique for investigating a variety of biological phenomena that produce changes in molecular proximity. The embodiments of the compounds, or the salts or conjugates thereof, may function as either a FRET donor or a FRET acceptor. In certain embodiments, they are FRET acceptors.

In one aspect, a fluorescing molecular complex, is provided, comprising:

a donor dye capable of absorbing light at a first wavelength and emitting excitation energy in response; and an acceptor dye capable of absorbing the excitation energy emitted by the donor dye and fluorescing at a second wavelength in response;

wherein either said donor dye or said acceptor dye has the structure of Formula I, II, III, IV, V, VI, or VII or a salt or conjugate thereof, as further described herein.

In specific embodiments, the donor dye or the acceptor dye has the structure of Formula III, or a salt or conjugate thereof.

In some embodiments, the acceptor dye has the structure of Formula III, or a salt or conjugate thereof. In some such embodiments, the acceptor dye has an excitation wavelength of between about 400 nm and about 900 nm. In further embodiments, the acceptor dye has an emission wavelength that is at least 30 nm, sometimes 50 nm, and preferably 70 nm greater than the excitation wavelength. In some embodiments, the acceptor dye has a Stokes shift of about 30 nm to about 250 nm, sometimes about 50 nm to about 225 nm, preferably about 70 nm to about 200 nm.

In further embodiments, the donor dye is a suitably functionalized quantum dot (QD) nanocrystal or a conjugate thereof, and the acceptor dye is one of the compounds described herein, or a salt or conjugate thereof. In some such embodiments, the acceptor dye is a compound of Formula III, or a salt or conjugate thereof.

In some embodiments, the acceptor dye is LSS-Cy or LSS-BA, or a salt or conjugate thereof. In some such embodiments, the acceptor dye is a conjugate of LSS-Cy or LSS-BA, or a salt thereof. In specific embodiments, the acceptor dye is LSS-Cy or LSS-BA conjugated to a nucleoside polyphosphate (e.g., deoxyguanosine tetraphosphate (dG4P), deoxyadenosine tetraphosphate (dA4P), deoxythymidine tetraphosphate (dT4P), deoxycytidine tetraphosphate (dC4p), etc.).

The compounds described herein may be isolated as salts where an ionizable acidic or basic group is present. Methods of forming and exchanging salts are well known in the art. For example, salts of acidic groups may be formed by reaction with organic or inorganic bases, and salts of basic groups may be formed by reaction with organic or inorganic acids. The formation of salts, including the number and nature of counterions present, will depend on the pH of the solution, the reagents used, and the functional groups present in the molecule.

Examples of inorganic bases include, but are not limited to, the hydroxides, alkoxides, carbonates, acetates and the like, of alkali metals (e.g., sodium, potassium or lithium) or alkaline earth metals (e.g., calcium), as well as similar salts of aluminum, ammonium, etc. Reaction of carboxylic acids or sulfonic acids with such inorganic bases provide the corresponding alkali metal salt or alkaline earth metal salt of the carboxylic or sulfonic acid. Such groups may be represented herein as $SO_3^-M^+$ or $CO_2^-M^+$, where $M^+$ represents the metal counterion.

Examples of organic bases that could be used include, but are not limited to, trimethylamine, triethylamine, pyridine, picoline, ethanolamine, diethanolamine, triethanolamine, dicyclohexylamine, N,N'-dibenzylethylenediamine, etc.

Examples of inorganic acids that could be used include, but are not limited to, hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In some embodiments, the acidic functional groups (i.e., carboxylic or sulfonic acids) that can be present as part of substituent groups $R^1$, $R^2$, $R^3$, $R^4$, as well as optional substituents present as part of $R^5$, $R^6$, or the tether linking them, will be protonated. In some embodiments, an inner salt (or zwitterion) will be formed between the positively charged nitrogen atom of the indolinium ring and the acidic functional group present on the attached substituent, e.g., $R^3$ in the tautomer shown in Formulae I-VI. At sufficiently low pH, all of the acidic groups can be protonated and the positive charge on the indolinium ring nitrogen can be counterbalanced by an anionic counterion, such as a halide ion or a sulfonate ion, etc. At higher pH, some or all of the acidic groups present in the various embodiments of the compounds described herein will be deprotonated, and the resulting negative charge(s) balanced by one or more positively charged counterions, such as alkali or alkaline earth metal ions.

Synthesis of LSS Dyes

Exemplary methods for preparing LSS heptamethine cyanine dyes from a 2-chloro-cyclohexene precursor are shown in Scheme 1 and Scheme 2. However, it should be understood that preparing the various embodiments of the LSS heptamethine cyanine dyes disclosed herein may be achieved using other methods known in the art. Synthetic methods for making selected compounds disclosed herein are also provided.

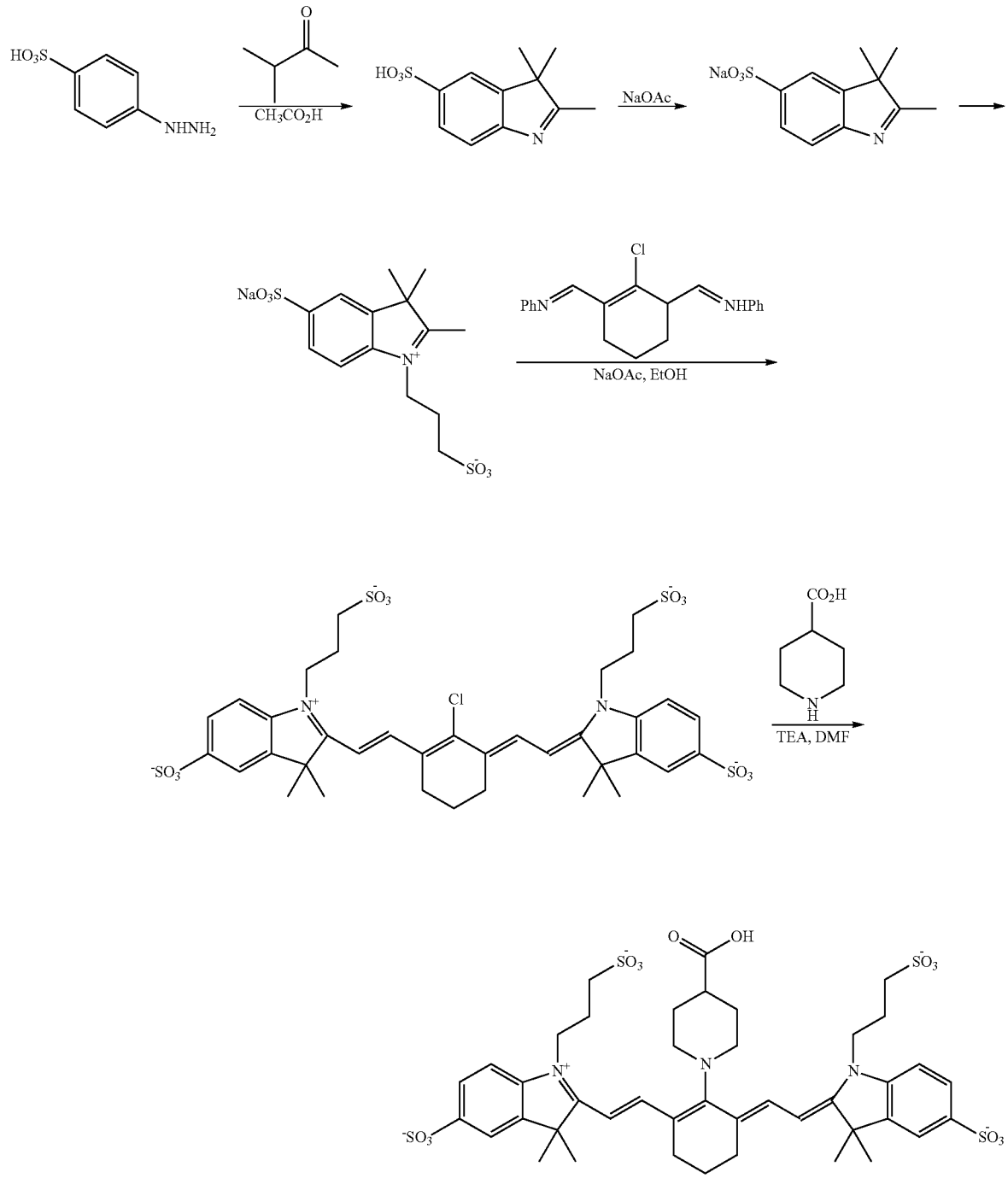

Scheme 1. Preparation of LSS-Cy Dye

Scheme 2. Preparation of LSS-BA dye

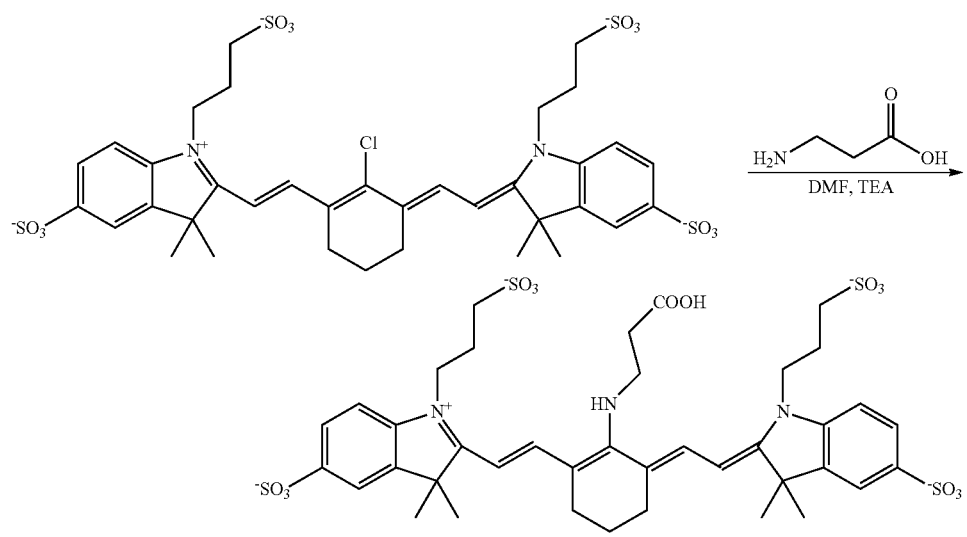

Conjugates

The various embodiments of the compounds described herein may be used to prepare a variety of dye conjugates. A dye conjugate can be formed by linking an embodiment of the LSS heptamethine cyanine dyes described herein to another moiety under conditions known to those of skill in the art. Frequently, the various embodiments of the LSS heptamethine cyanine dye compounds disclosed herein are conjugated through a functional group that is present as an optional substituent on the $C_{1-6}$ alkyl groups at $R^5$ and $R^6$, or as part of a substituent on the ring formed when $R^5$ and $R^6$ are taken together. Examples of functional groups useful in such conjugation reactions include halo, acyl, heteroacyl, carboxylic acid, primary or secondary amine, thiol, hydroxyl, or activated derivatives thereof. When $R^5$ and $R^6$ are taken together to form a ring, the functional group may be directly attached to the ring, or may be a substituent on a $C_{1-6}$ alkyl substituent thereon. In addition to stable activated derivatives, such as the NHS, HOBt and HOAt esters described previously, the functional groups described herein may be transiently activated to undergo in situ conjugation, for example by reaction with a coupling reagent such as a carbodiimide or a uronium phosphate reagent (e.g., HBTU).

In some embodiments, the compounds described herein may be directly conjugated to an appropriately selected moiety, for example, by formation of an amide bond between a carboxylic acid or an amine functional group on the dye molecule with a corresponding amine or acid functional group on the moiety to be conjugated. In other embodiments, the dye may be coupled to the appropriately selected moiety via an intermediate linker. The linker may be attached to a functional group on the dye or to the other moiety prior to conjugation. In frequent embodiments, the linker comprises a saturated or unsaturated alkylene or heteroalkylene group. For example, a carboxylic acid on the dye can be coupled to linker molecule comprising an aminoalkanol to form an amide bond, and the hydroxyl group of the alkanol can be further coupled to the desired moiety.

Examples of suitable moieties to which the compounds described herein may form conjugates include, without limitation, nucleotides, nucleosides, nucleic acids, oligonucleotides, deoxyoligonucleotides, DNA fragments, RNA fragments, or a derivatized variant of one of these. Additional examples of conjugatable moieties include antibodies, amino acids, peptides, and proteins, as well as haptens, antigens, drugs, cells or viruses, carbohydrates, polysaccharides and oligosaccharides, lipids, phospholipids, lipoproteins, lipopolysaccharides, liposomes, polymers, polymeric microparticles, etc.

In some embodiments, the other moiety can be an affinity molecule, such as an antibody, receptor or enzyme, which specifically recognizes, binds to or modifies another compound or structure. The dye conjugate, by virtue of the affinity molecule, can be used to detect, for example, the presence and/or quantity of biological and chemical compounds, interactions in biological systems, biological processes, alterations in biological processes, or alterations in the structure of biological compounds. The affinity molecule, when linked to a dye compound described herein, can interact with a biological target that serves as the second member of the binding pair, in order to detect biological processes or reactions, or to alter biological molecules or processes. The interaction of the affinity molecule and the biological target may involve specific binding, and can involve covalent, noncovalent, hydrophobic, hydrophilic, electrostatic, van der Waals, magnetic, or other interactions.

The affinity molecule or other moiety associated with a dye can be naturally occurring or artificially synthesized, and can be selected to have a desired physical, chemical or biological property. Such properties can include covalent and noncovalent association with, for example, signaling molecules, prokaryotic or eukaryotic cells, viruses, subcellular organelles and any other biological compounds. Other properties include the ability to affect a biological process, cell cycle, blood coagulation, cell death, transcription, translation, signal transduction, DNA damage or cleavage, production of radicals, scavenging radicals, the ability to alter the structure of a biological compound, crosslinking, proteolytic cleavage, and radical damage.

In some embodiments, one of the LSS dye compounds described herein may be conjugated to a molecule or species for detection by means of FRET. In some embodiments, the FRET efficiency in a FRET reaction of the compounds described herein can be between about 25% to about 100%.

FRET refers to Fluorescence Resonance Energy Transfer (sometimes called Forster Resonance Energy Transfer) which is the basis of various fluorescence measuring techniques that allow detection of the close proximity of two appropriately labeled molecules or species. As discussed above, in FRET, a donor label non-radiatively transfers energy to a second acceptor label. The acceptor may be a fluorophore which may then emit a photon. Donor-acceptor pairs are typically selected such that there is overlap between the emission spectrum of the donor and excitation spectrum of the acceptor. In some applications, the acceptor may be a quencher.

FRET efficiency depends sharply on donor-acceptor distance r as $1/r^6$. The distance where FRET efficiency is 50% is termed $R_0$, also known as the Forster distance. $R_0$ is unique for each donor-acceptor combination and may be 5 to 10 nm. In biological applications, FRET can provide an on-off type signal, indicating when the donor and acceptor are within $R_0$ of each other. Additional factors affecting FRET efficiency include the quantum yield of the donor, the extinction coefficient of the acceptor, and the degree of spectral overlap between donor and acceptor. FRET efficiency and signal detection is described in D. W. Piston and G. J. Kremers, Trends Biochem. Sci. 32:407 (2007).

Nanocrystals have been used for FRET detection in biological systems. See, e.g., Willard et al., 2001, *Nano. Lett.* 1:469; Patolsky F. et al., 2003, *J. Am. Chem. Soc.* 125:13918; Medintz I. L. et al., 2003, *Nat. Mater.* 2:630; Zhang C. Y., et al., 2005, *Nat. Matter.* 4:826. Nanocrystals may be advantageous because their emission may be size-tuned to improve spectral overlap with an acceptor or quencher. Nanocrystals in general have high quantum yield and are less susceptible to photobleaching than other types of FRET donors.

In some embodiments, the compounds described herein, or a salt or conjugate thereof, functions as a FRET acceptor. In particular embodiments, the corresponding FRET donor is a suitably functionalized quantum dot (QD) nanocrystal.

In a particular embodiment the FRET donor is a QD605 nanocrystal, or a conjugate thereof. When QD605 is used as the FRET donor, the reddest acceptor channel is limited to the emission window of 750-800 nm. Most commercial dyes having emission in this window (e.g., AF750, Cy7, HiLyte 750, CF 750, Atto 750, Dy734 and Dy750) have a very small absorption around 605 nm (extinction coefficient ~15,000 $M^{-1}cm^{-1}$). For example, no FRET signal was observed from QD605 to AF750. By contrast, the LSS-Cy-dG4P and LSS-BA-dG4P dyes absorb strongly around 605 nm, which match the emission of QD605.

In specific embodiments, the LSS-Cy dye or the LSS-BA dye (prepared as described herein) is conjugated to a nucleoside polyphosphate (e.g., deoxyguanosine tetraphosphate (dG4P), deoxyadenosine tetraphosphate (dA4P), deoxythymidine tetraphosphate (dT4P), deoxycytidine tetraphosphate (dC4P), etc.) as shown in Scheme 3 and Scheme 4, respectively. The carboxylic acid present in the dye molecule was converted to an activated NHS ester, and then further reacted with a nucleophilic amine and linked to dG4P to provide the conjugates shown.

Scheme 3. Conjugation of LSS-Cy dye to dG4P via intermediate NHS ester

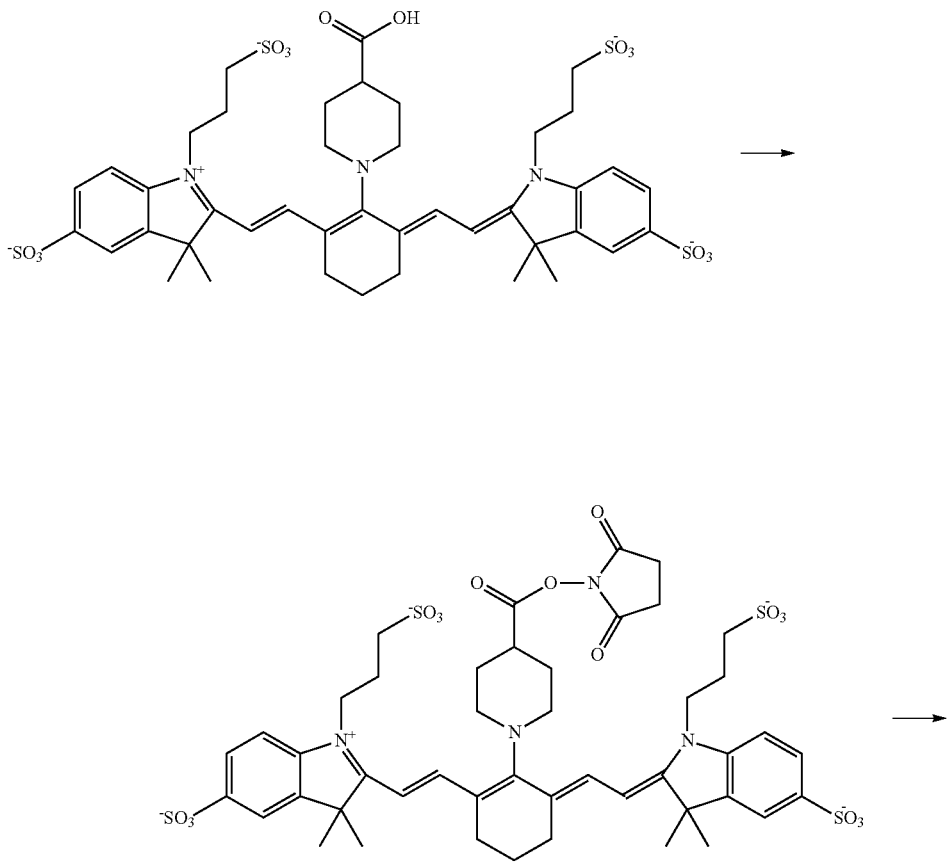

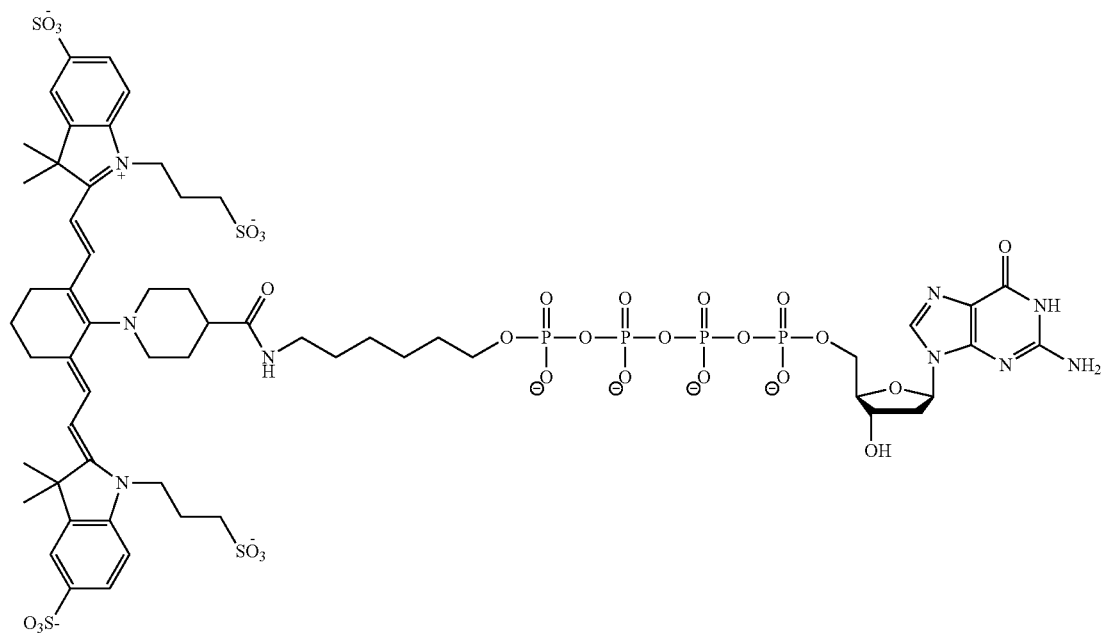
Scheme 4. Conjugation of LSS-BA dye to dG4P via intermediate NHS ester
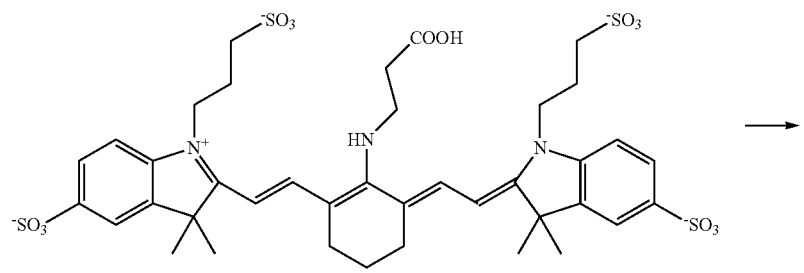
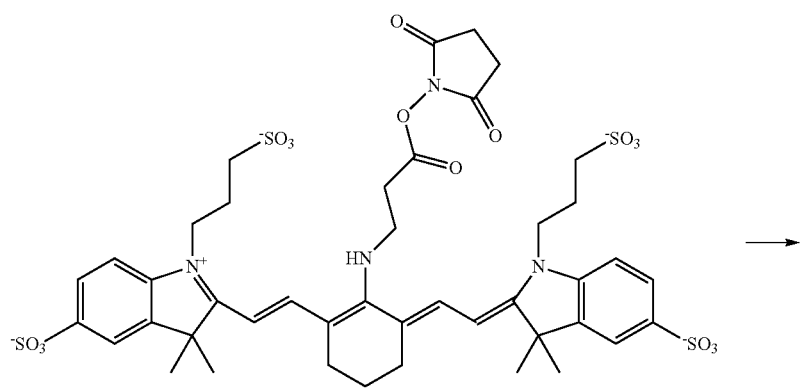

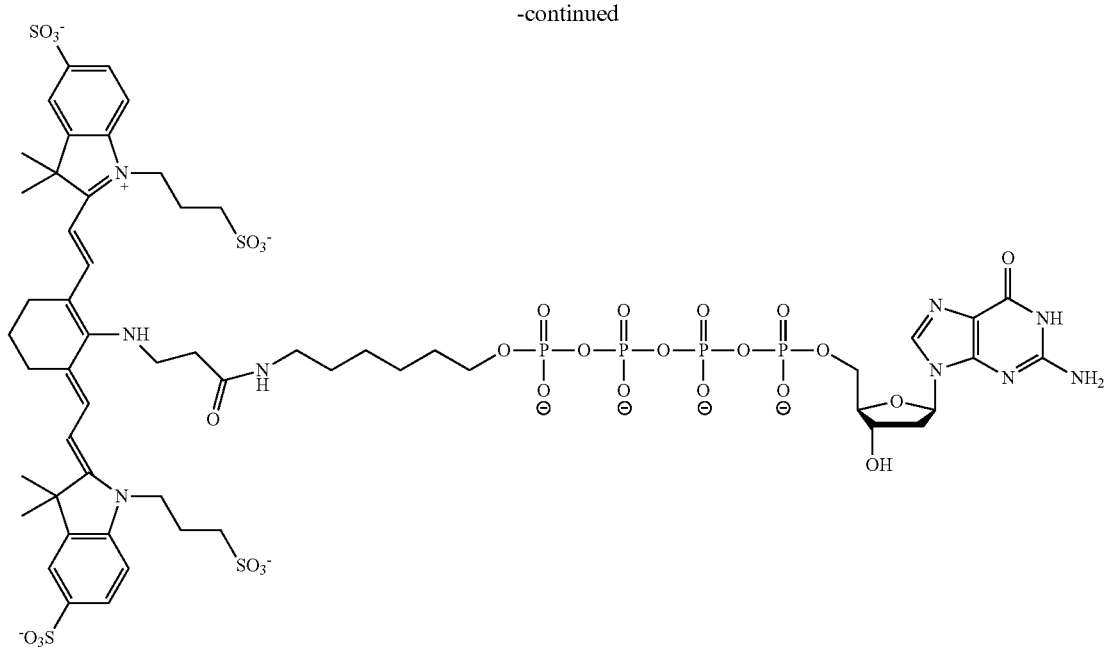

The following experimental results are offered to illustrate but not to limit the embodiments described herein.

EXAMPLE 1

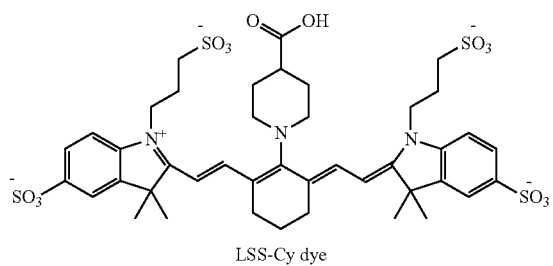

LSS-Cy dye

The LSS-Cy dye was prepared as shown in Scheme 1 and detailed in the following experimental synthesis workflow.

1. Synthesis of Compound 3:

Compound 1 (i.e., 5-sulfo-1-sulfopropyl-2,3,3-trimethyl-indoleninium, inner salt, sodium salt) (1 g), compound 2 (i.e., N-[(3-(anilinomethylene)-2-chloro-1-cyclohexen-1-yl)methylene]aniline monohydrochloride) (404 mg) and NaOAc (226 mg) in absolute EtOH (30 mL) were refluxed for 5 hours. After cooling, the precipitates were collected by filtration and washed with EtOH (30 mL×4) and CHCl3 (30 mL×4). The solid was purified by column chromatography on silica gel, eluting with 10% H2O in acetonitrile. Evaporation of the solvent afforded compound 3 as a green solid (350 mg).

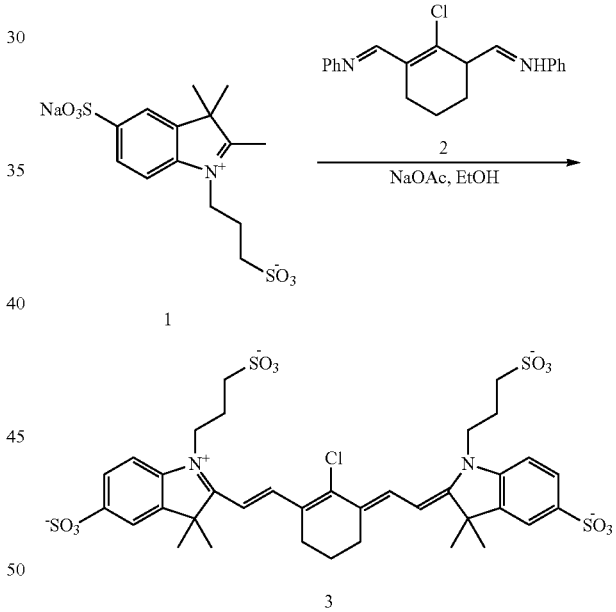

2. Synthesis of Compound 5 (LSS-Cy dye):

Compound 3 (i.e., 2-[2-[2-Chloro-3-[2-[5-sulfo-1,3-di-hydro-3,3-dimethyl-1-(4-sulfopropyl)-2H-indol-2-ylidene]-ethylidene]-1-cyclohexen-1-yl]-ethenyl]-5-sulfo-3,3-dim-ethyl-1-(4-sulfopropyl)-3H-indolium) (100 mg), 4 (i.e., isonipecotic acid) (150 mg) and triethylamine (175 µL) were dissolved in a mixture of DMF (3 mL) and water (2 mL). The solution was heated at about 80-85° C. for about 2 hours. The solvent was evaporated and the residue was purified by column chromatography (C.C.) on silica gel, eluting with 10% water/acetonitrile. The product was further purified by C.C. on sephadex LH-20, eluting with H2O. Evaporation of the solvent gave ca. 70 mg of compound 5.

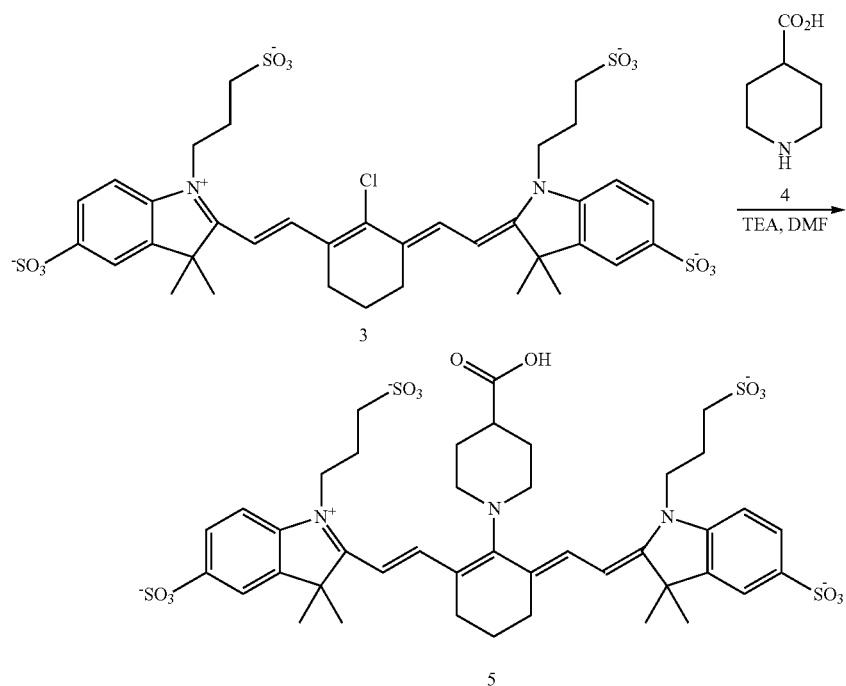
The emission spectrum of LSS-Cy was similar to AlexaFluor 750 (AF750). The LSS-Cy dye absorbed strongly at 605 nm ($\epsilon = 66000$ M$^{-1}$cm$^{-1}$).
Quantum Yield: 0.72 times of that of AF750.
Brightness: ca. 3.5 times of that of AF750 when excited at 605 nm.
EXAMPLE 2
LSS-Cy-dG4P Conjugate
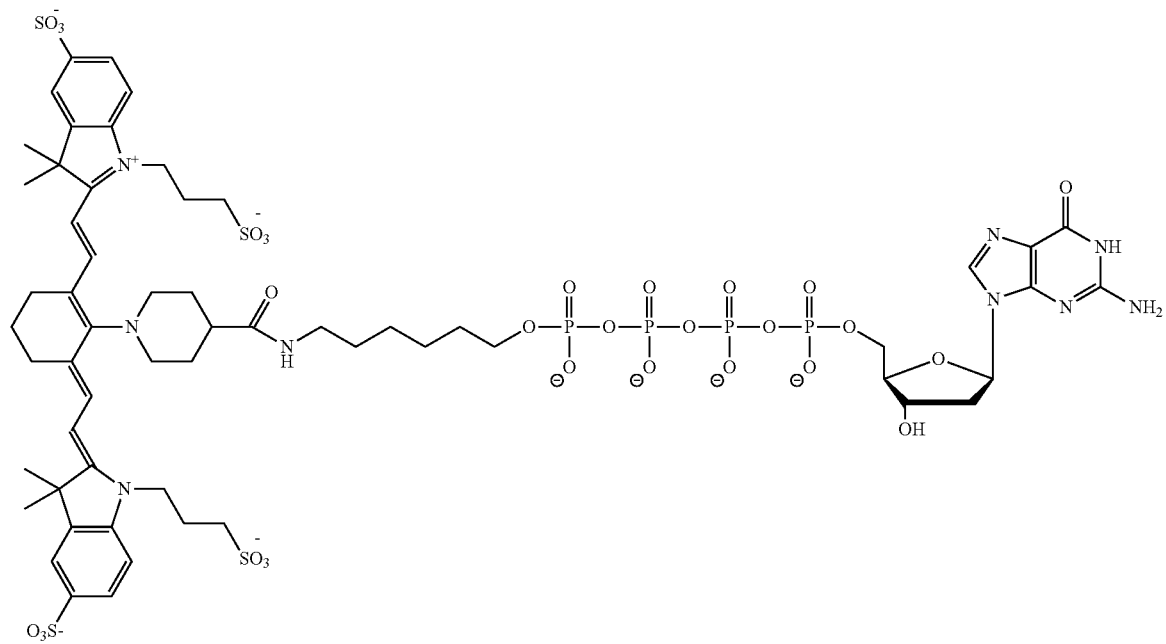

The LSS-Cy dye was conjugated to dG4P via its NHS ester, as shown in Scheme 3 and detailed in the following experimental synthesis workflow.

3. Synthesis of Succinate Ester (SE) Form of Compound 5 (Compound 7)

To a solution of compounds 5 (40 mg) and 6 (27 mg) in dry dimethylformamide (DMF) (5 mL) was added triethylamine (100 µL). The solution was stirred at room temperature for 1 h. Ethyl ether (ca. 30 mL) was slowly added. The precipitate was collected by centrifuge and dried in vacuum (42 mg).

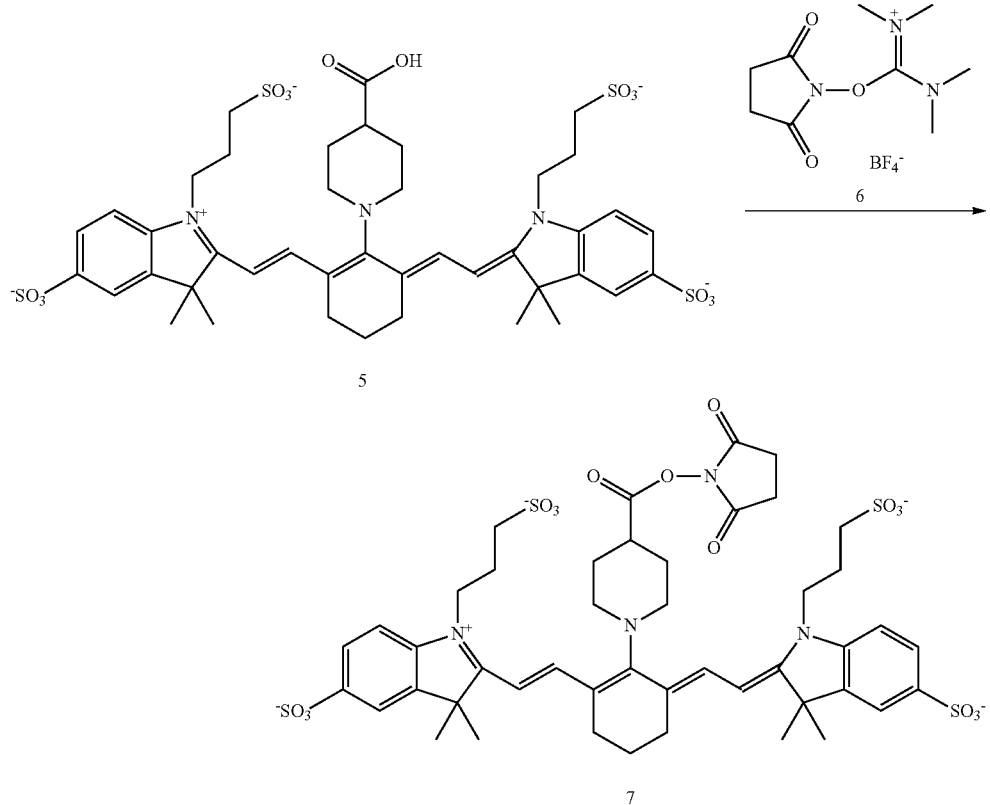

4. Labeling dGP4 with LSS-Cy Dye.

A solution of amino-dG4P (10) (0.5 mg) in DMF-water (2:1, 300 µL) was mixed with 50 µL of saturated sodium bicarbonate solution. To this solution was added the LSS-Cy dye SE (7) (2 mg). The solution was stirred at room temperature until the completion of the reaction (ca. 1 hour). The product was purified by column chromatography on sephadex LH-20, eluting with water. The desired fraction was concentrated to ca. 300 µL and stored at −20° C.

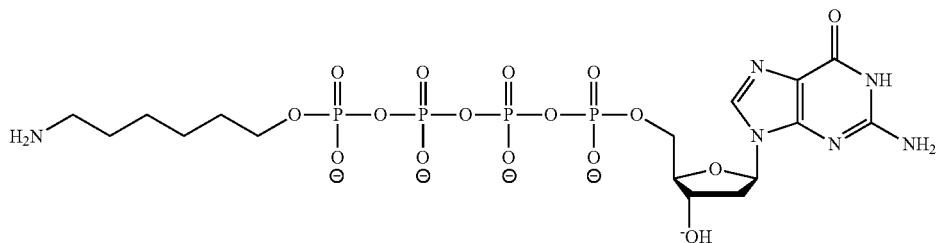

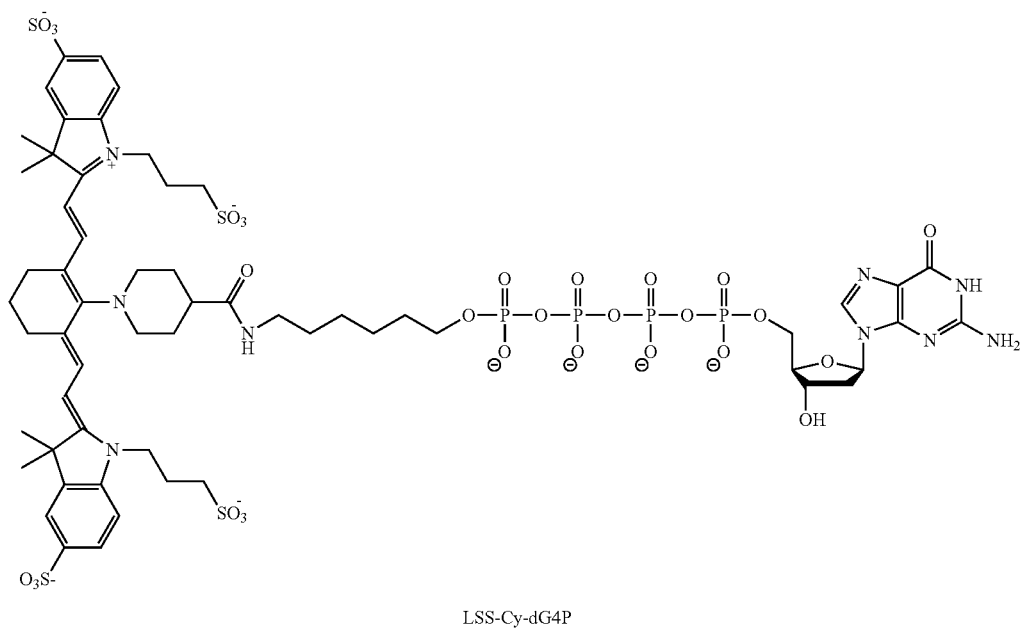

LSS-Cy-dG4P

After conjugation, the absorption spectra of the LSS-Cy-dG4P conjugate shifted to longer wavelength (from 575 nm to 590 nm).

The excitation and emission spectra remained the same, but the quantum yield was increased 1.1 times.

EXAMPLE 3

LSS-BA Dye

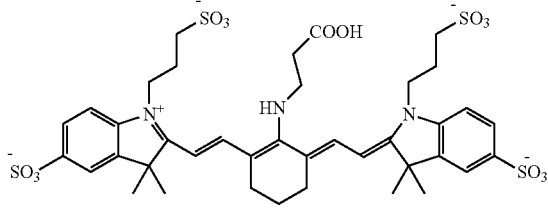

The LSS-BA dye was prepared as shown in Scheme 2 and detailed in the following experimental synthesis workflow.

1. Synthesis of Compound 8 (LSS-BA Dye)

Compound 3 (i.e., 2-[2-[2-Chloro-3-[2-[5-sulfo-1,3-dihydro-3,3-dimethyl-1-(4-sulfopropyl)-2H-indol-2-ylidene]-ethylidene]-1-cyclohexen-1-yl]-ethenyl]-5-sulfo-3,3-dimethyl-1-(4-sulfopropyl)-3H-indolium) (50 mg), β-alanine (52 mg) and triethylamine (76 μL) were dissolved in a mixture of DMF (2 mL) and water (1 mL). The solution was heated at about 80-85° C. for about 2 hours. The solvent was evaporated and the residue was purified by column chromatography (C.C.) on silica gel, eluting with 10% water/acetonitrile. The product was further purified by C.C. on sephadex LH-20, eluting with H2O. Evaporation of the solvent gave ca. 22 mg of compound 8.

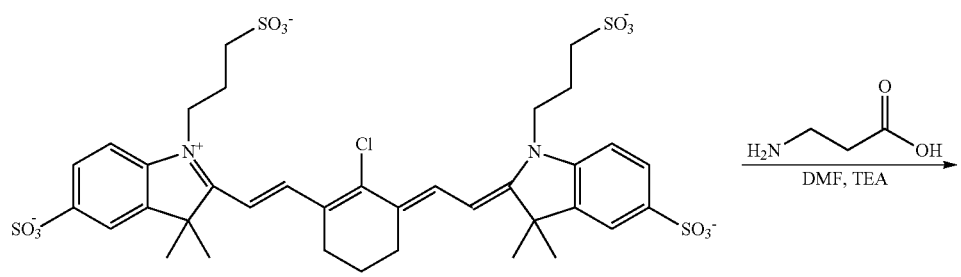

3

-continued

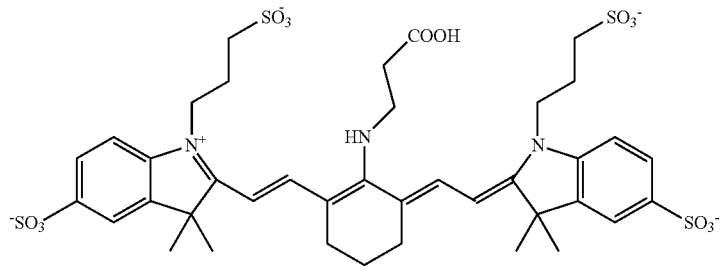

8

The LSS-BA dye absorbed strongly at 601 nm ($\epsilon$=92000 $M^{-1}cm^{-1}$), and emitted at 760 nm with a broad peak.

Quantum Yield: 1.55 times of that of AF750.

Brightness: ca. 11 times of that of AF750 when excited at 605 nm.

EXAMPLE 4

LSS-BA-dG4P Conjugate

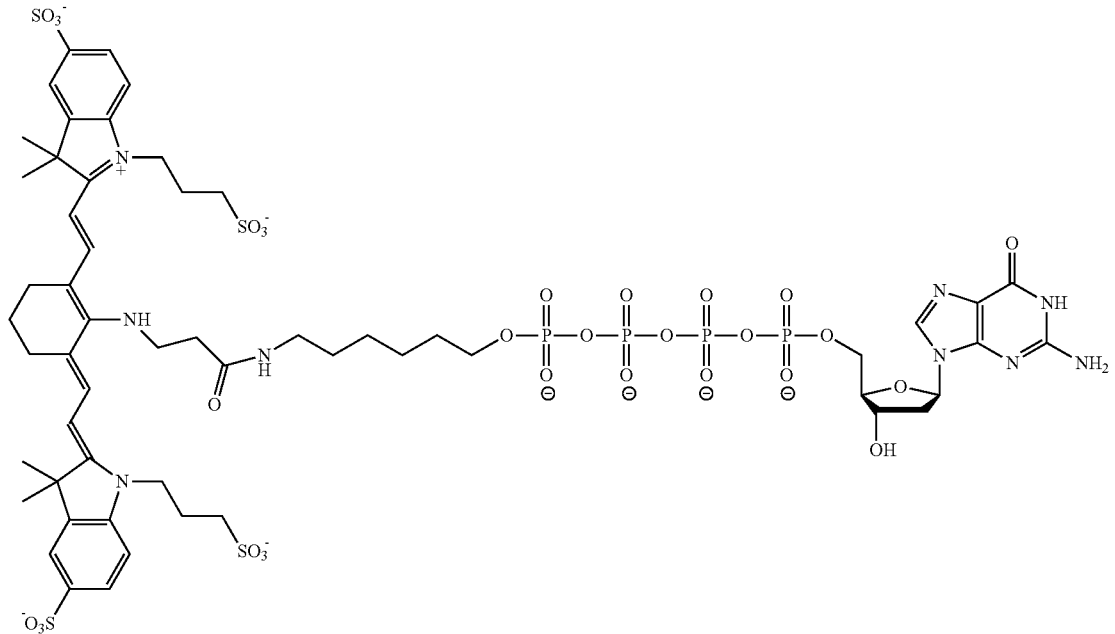

The LSS-BA dye was conjugated to dG4P via its NHS ester, as shown in Scheme 4 and detailed in the following experimental synthesis workflow.

2. Synthesis of SE of Compound 8 (Compound 9)

To a solution of compounds 8 (10 mg) and 6 (11 mg) in dry DMF (5 mL) was added triethylamine (50 µL). The solution was stirred at room temperature for 1 h. Ethyl ether (ca. 30 mL) was slowly added. The precipitate was collected by centrifuge and dried in vacuum (14 mg).

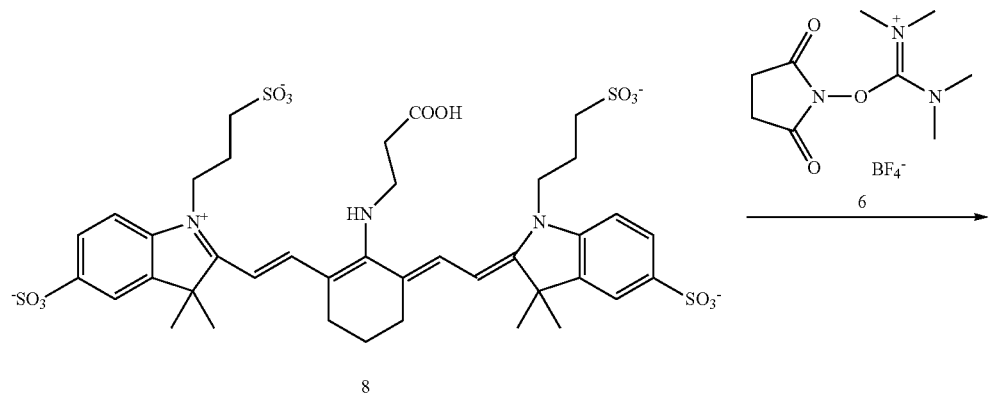

3. Labeling dGP4 with LSS-BA Dye.

A solution of amino-dG4P (10) (0.5 mg) in DMF-water (2:1, 300 μL) was mixed with 50 μL of saturated sodium bicarbonate solution. To this solution was added the LSS-BA dye SE (9) (2 mg). The solution was stirred at room temperature until the completion of the reaction (ca. 1 hour). The product was purified by column chromatography on sephadex LH-20, eluting with water. The desired fraction was concentrated to ca. 300 μL and stored at −20° C.

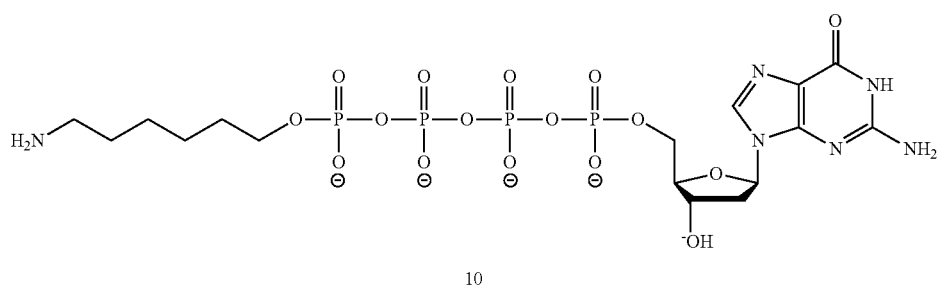

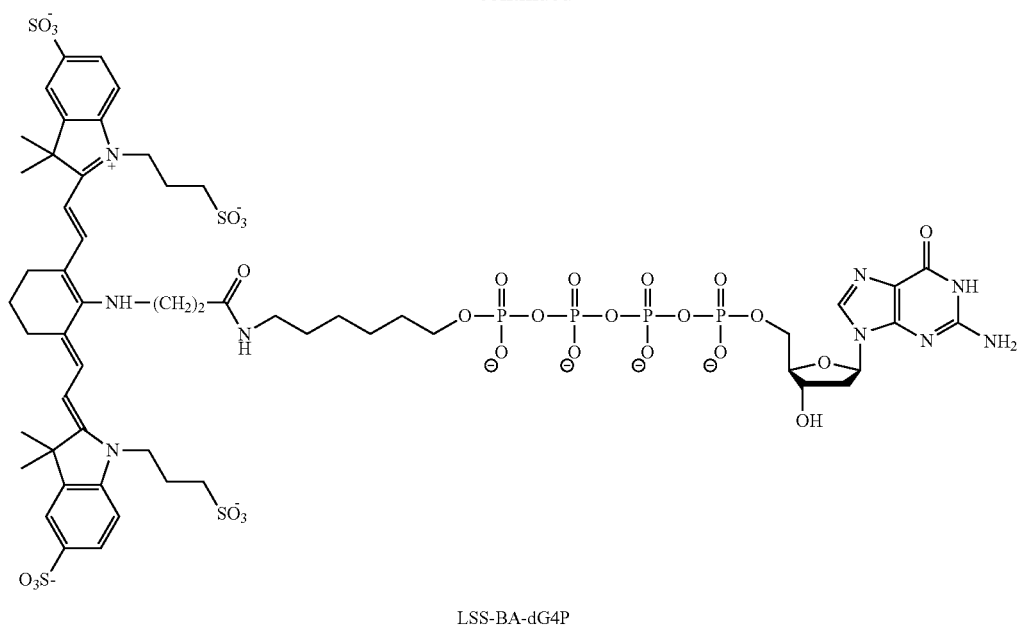

LSS-BA-dG4P

After conjugation with dG4P, the absorption of the dye conjugate shifted to longer wavelength (from 600 nm to 617 nm).

The excitation and emission spectra remained the same following conjugation, but the quantum yield increased by 1.05 times.

By way of example, the amino-dG tetraphosphate (i.e., nucleoside polyphosphate moiety) that the LSS-Cy and LSS-BA dyes were depicted above as being conjugated to (in schemes 3 and 4) was prepared as shown in the following experimental synthesis workflow.

EXAMPLE 5

Amino-dG Tetraphosphate

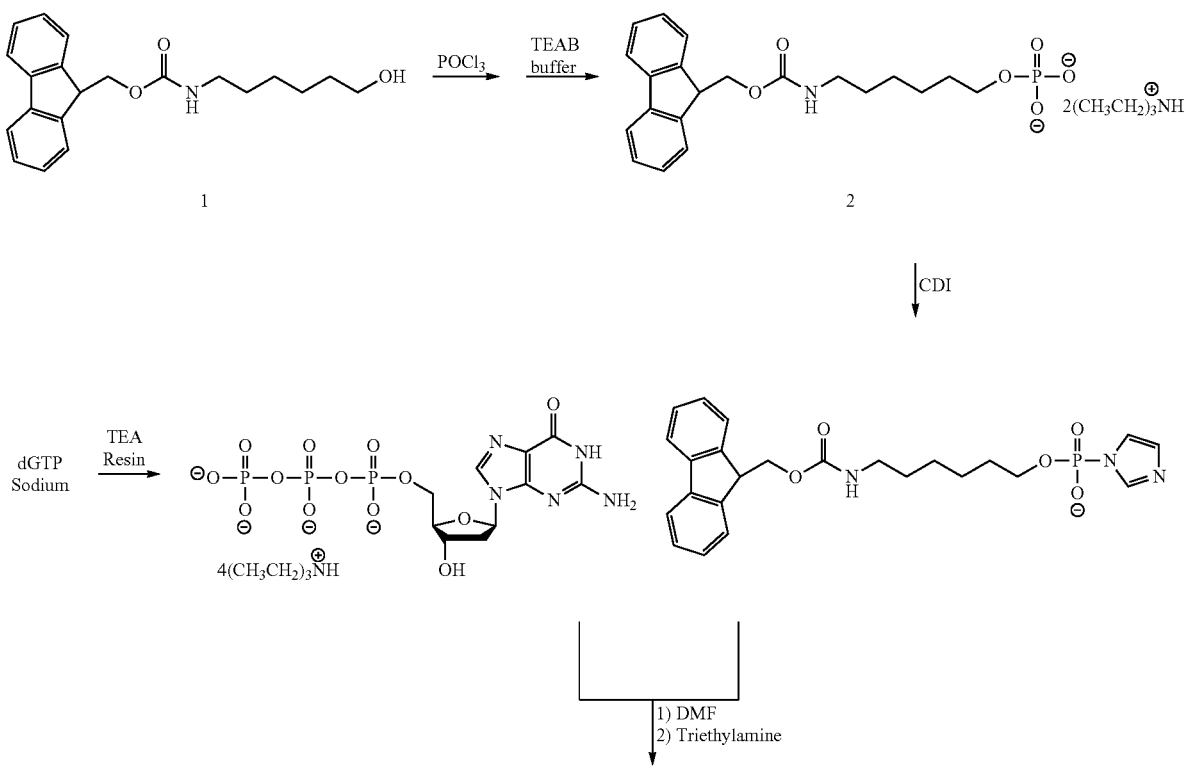

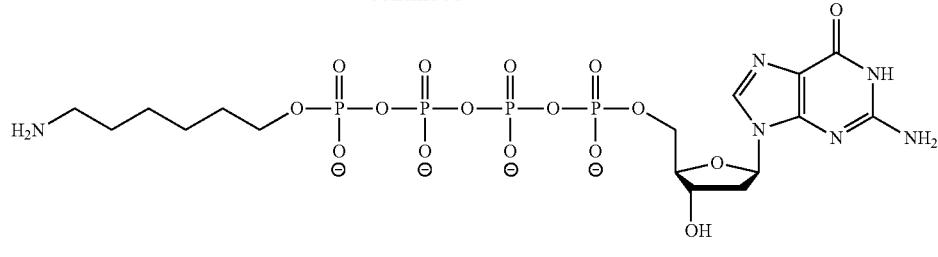

3

1. Synthesis of Compound 2.

Compound 1 (678 mg, 2 mmol) was suspended in trimethyl phosphate (5 mL) and cooled to 0° C. POCl3 (280 μL) was added to the stirred mixture under argon. The mixture was warmed up and stirred at room temperature overnight. The reaction was quenched by adding slowly 4 mL of TEAB buffer (1 M) at about 0° C. Triethylamine was added to adjust the pH to pH 7.0. The solvent was evaporated and the residue was purified by column chromatography on silica gel, eluting with 10% H2O/CH3CN. After evaporation of the solvent, the solid was dissolved in water. The pH of the solution was adjusted to pH 7 with TEAB buffer (1 M), followed by co-evaporation with methanol. Yield: 400 mg of compound 2.

LSS-BAS, LSS-AL, LSS-SAR, LSS-GL, LSS-ALS, LSS-CY LITE, LSS-SER (Abs. 628 nm/em 745 nm, QY=1.36 LSS-BA), LSS-HS (Abs. 597 nm/em. 755 nm, QY=1.0 LSS-BA), LSS-TH (Abs. 637 nm/em. 728 nm, QY=2.0 LSS-BA), LSS-AB (Abs. 623 nm/em. 757 nm, QY=1.1 LSS-BA), LSS-VA (Abs. 628 nm/em. 722 nm, QY=1.1 LSS-BA), LSS-PP (Abs. 612 nm/em. 780 nm), LSS-GL-GL (Abs. 642 nm/em. 760 nm), LSS-CER-CY (Abs. 700 nm/em. 770 nm), and LSS-GL-CY dyes (Abs. 635 nm/em. 760 nm) were made by the same method as the LSS-BA and LSS-CY dyes (see Example 1 and Example 3 above).

Unless otherwise specified, all documents referred to herein are incorporated by reference in their entirety.

While certain embodiments have been described above, it will be understood that the embodiments are described by way of example only. Those skilled in the art will appreciate that the same can be performed within a wide range of equivalent parameters, concentrations, and conditions without departing from the spirit and scope of the embodiments disclosed herein and without undue experimentation. Accordingly, the compositions/compounds, processes and/or methods described herein should only be limited in light of the claims that follow when taken in conjunction with the above description and accompanying drawings.

The invention claimed is:

1. A compound of Formula I or II:

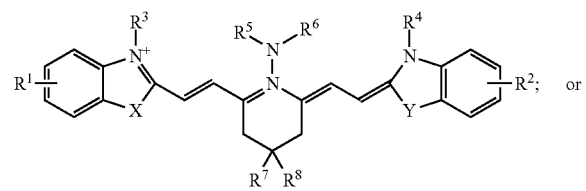

I

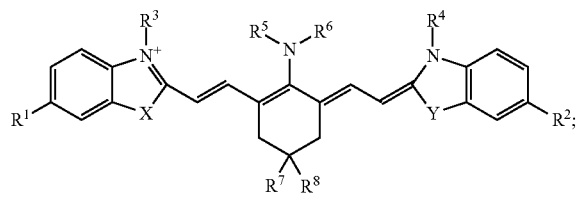

II or a salt thereof;

wherein $R^1$ and $R^2$, when taken alone, are independently, halo, hydroxyl, amino, $C_{1-6}$ alkylamino, $C_{2-12}$ dialkylamino, $C_{1-6}$ perfluoroalkyl, $C_{1-6}$ alkyl, or $C_{1-6}$ alkoxy;

$R^3$ and $R^4$ are $(CH_2)_3SO_3H$;

$R^5$ and $R^6$, when taken alone, are independently H, $C_{1-6}$ carbonyl or substituted $C_{1-6}$ alkyl, wherein at least one of $R^5$ and $R^6$ is $C_{1-6}$ alkyl substituted with a substituent selected from the group consisting of $SO_3H$, COOH, OH, and $NH_2$, maleimide, thiol, isocyanate, isothiocyanate, disulfide, alkynyl, azidoyl and trialkoxysilane;

$R^7$ and $R^8$ are independently H, $C_{1-4}$ alkyl, or phenyl;

X and Y are independently $CR^9_2$, $NR^{10}$, O or S; and each $R^9$ and $R^{10}$ is independently $C_{1-4}$ alkyl.

2. A compound of Formula III:

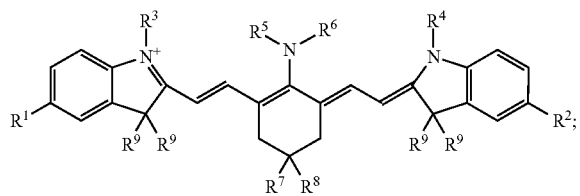

III or a salt thereof;

wherein $R^1$ and $R^2$, when taken alone, are independently, halo, hydroxyl, amino, $C_{1-6}$ alkylamino, $C_{2-12}$ dialkylamino, $C_{1-6}$ perfluoroalkyl, $C_{1-6}$ alkyl, or $C_{1-6}$ alkoxy;

$R^3$ and $R^4$ are $(CH_2)_3SO_3H$;

$R^5$ and $R^6$, when taken alone, are independently H, $C_{1-6}$ carbonyl or substituted $C_{1-6}$ alkyl, wherein at least one of $R^5$ and $R^6$ is $C_{1-6}$ alkyl substituted with a substituent selected from the group consisting of $SO_3H$, COOH, OH, and $NH_2$, maleimide, thiol, isocyanate, isothiocyanate, disulfide, alkynyl, azidoyl and trialkoxysilane;

$R^7$ and $R^8$ are independently H, $C_{1-4}$ alkyl, or phenyl; and each $R^9$ is independently $C_{1-4}$ alkyl.

3. The compound of claim 2, wherein each $R^9$ is methyl.

4. The compound of claim 2, wherein each of $R^7$ and $R^8$ is H.

5. The compound of claim 2, wherein each of $R^1$ and $R^2$ is $SO_3H$.

6. The compound of claim 2 which has a Stokes shift of about 30 nm to about 250 nm.

7. The compound of claim 2 which has a Stokes shift of about 50 nm to about 225 nm.

8. The compound of claim 2 which has a Stokes shift of about 70 nm to about 200 nm.

9. A compound selected from:

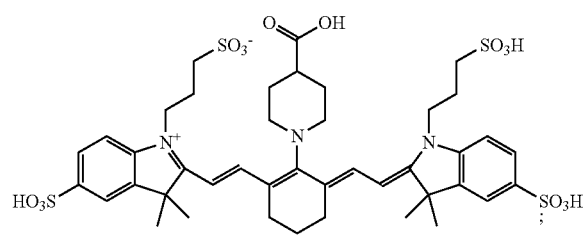

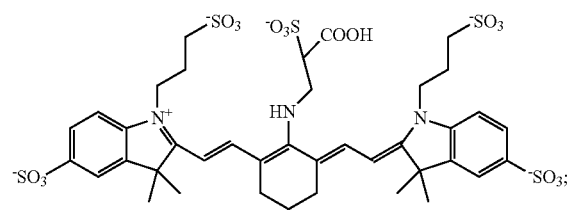

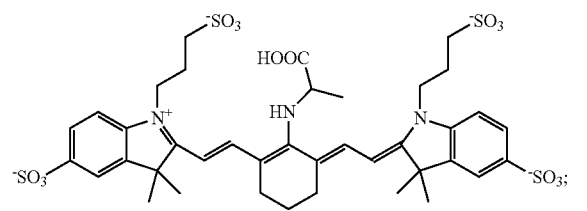

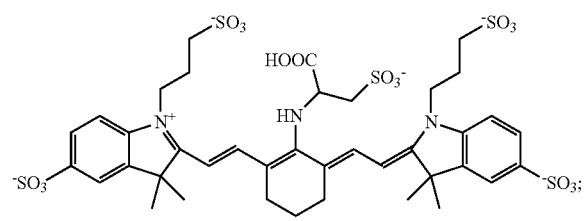

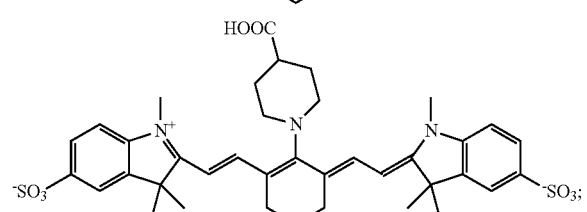

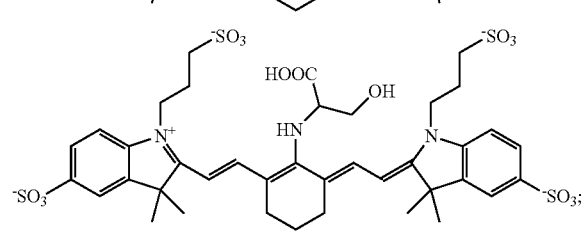

-continued

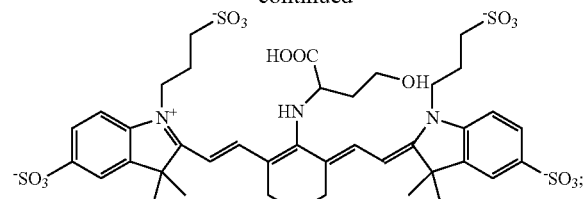

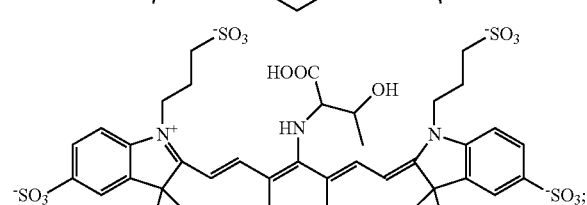

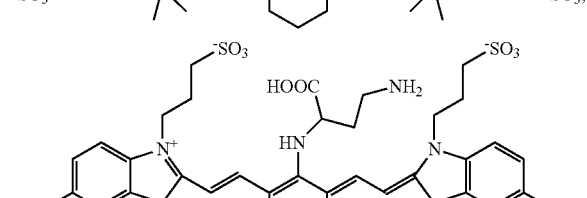

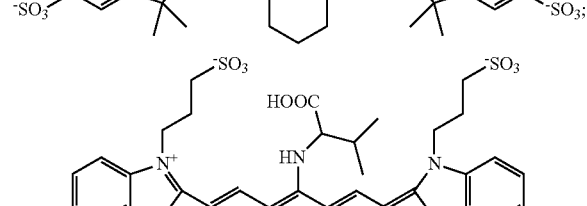

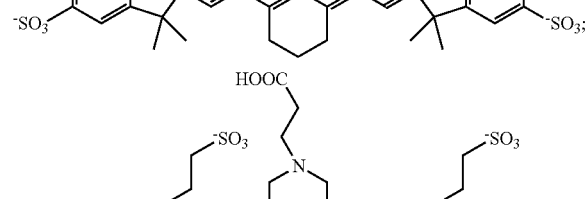

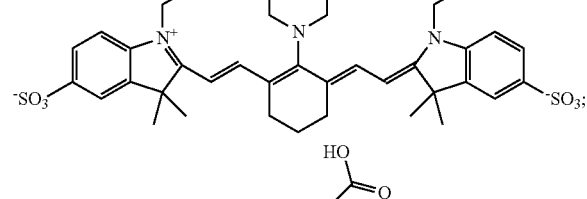

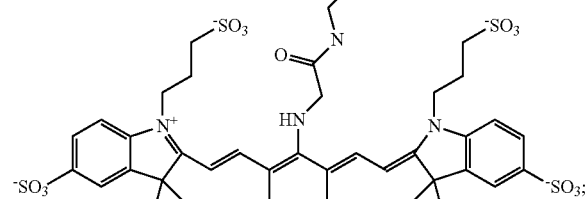

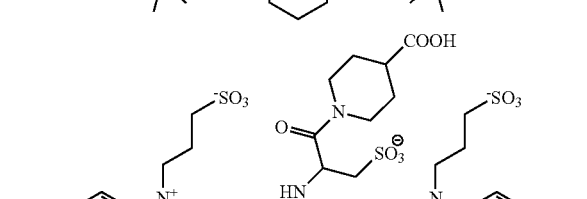

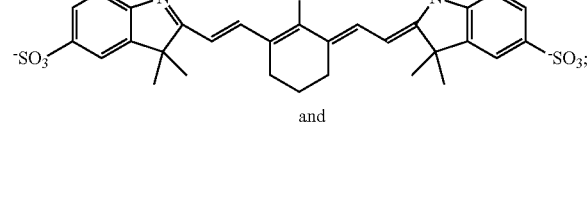

and

-continued

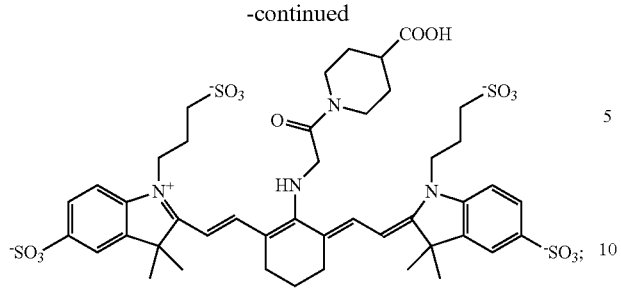

or a salt thereof.

10. The compound of claim 2 which is conjugated to a nucleotide, nucleoside, nucleic acid, oligonucleotide, deoxyoligonucleotide, DNA fragment, RNA fragment, or a derivatized variant of one of these; or an antibody, amino acid, peptide, or protein.

11. The compound of claim 2, wherein the compound has an excitation wavelength between 400 and 900 nm.

12. The compound of claim 11, wherein the compound has an emission wavelength that is at least 70 nm greater than the excitation wavelength.

13. A fluorescing molecular complex comprising:
a donor dye capable of absorbing light at a first wavelength and emitting excitation energy in response; and
an acceptor dye capable of absorbing the excitation energy emitted by the donor dye and fluorescing at a second wavelength in response;
wherein either said donor dye or said acceptor dye has the structure according to claim 2.

14. The donor dye or acceptor dye of claim 13 which has a Stokes shift of about 30 nm to about 250 nm.

15. The donor dye or acceptor dye of claim 13 which has a Stokes shift of about 50 nm to about 225 nm.

16. The donor dye or acceptor dye of claim 13 which has a Stokes shift of about 70 nm to about 200 nm.

17. The donor dye or acceptor dye of claim 13, wherein the compound has an excitation wavelength between 400 and 900 nm.

* * * * *

UNITED STATES PATENT AND TRADEMARK OFFICE
CERTIFICATE OF CORRECTION

PATENT NO. : 9,624,424 B2
APPLICATION NO. : 14/566166
DATED : April 18, 2017
INVENTOR(S) : Yi-Zhen Hu et al.

Page 1 of 1

It is certified that error appears in the above-identified patent and that said Letters Patent is hereby corrected as shown below:

Claim 1, Line 2, replace the structure of Formula I:

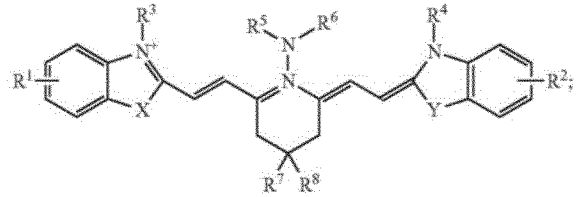

With the following structure:

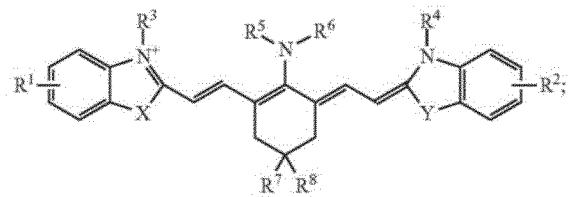

Signed and Sealed this
Eleventh Day of December, 2018

Andrei Iancu
*Director of the United States Patent and Trademark Office*